(12) United States Patent
Hayardeny-Nissimov et al.

(10) Patent No.: US 11,197,870 B2
(45) Date of Patent: Dec. 14, 2021

(54) TREATMENT FOR HEPATIC FIBROSIS

(71) Applicant: GALMED RESEARCH AND DEVELOPMENT LTD, Tel Aviv (IL)

(72) Inventors: Liat Hayardeny-Nissimov, Tel Aviv (IL); Tali Gorfine, Tel Aviv (IL); Allen Baharaff, Tel Aviv (IL); Jose M. Mato de la Paz, Getxo (ES)

(73) Assignee: Galmed Research and Development Ltd, Tel Aviv (IL)

( * ) Notice: Subject to any disclaimer, the term of this patent is extended or adjusted under 35 U.S.C. 154(b) by 0 days.

(21) Appl. No.: 15/789,564

(22) Filed: Oct. 20, 2017

(65) Prior Publication Data

US 2018/0125862 A1 May 10, 2018

Related U.S. Application Data

(60) Provisional application No. 62/475,129, filed on Mar. 22, 2017, provisional application No. 62/420,017, (Continued)

(51) Int. Cl.
*A61K 31/56* (2006.01)
*A61K 31/20* (2006.01)
(Continued)

(52) U.S. Cl.
CPC .......... *A61K 31/575* (2013.01); *A61K 9/0053* (2013.01); *A61K 45/06* (2013.01);
(Continued)

(58) Field of Classification Search
CPC .................................................. A61K 31/575
(Continued)

(56) References Cited

U.S. PATENT DOCUMENTS 6,384,024 B1 5/2002 Gilat
6,395,722 B1 5/2002 Gilat
(Continued)

FOREIGN PATENT DOCUMENTS

CA 3025671 12/2017
EP 2632925 5/2015
(Continued)

OTHER PUBLICATIONS

Wikipedia "Non-alcoholic fatty liver disease " 2018.*
(Continued)

*Primary Examiner* — Shengjun Wang
(74) *Attorney, Agent, or Firm* — Mark S. Cohen; Pearl Cohen Zedek Latzer Baratz

(57) ABSTRACT

The invention relates to the treatment and reduction of fibrosis, specifically hepatic fibrosis. More specifically, embodiments of the invention provide compositions and methods useful for the treatment and inhibition of hepato-fibrotic conditions associated with Non-Alcoholic Fatty Liver Disease (NAFLD) and Non-Alcoholic Steatohepatitis (NASH), employing the use of 3β-arachidylamido-7α,12α-dihydroxy-5β-cholan-24-oic acid (Aramchol) or a pharmaceutically acceptable salt thereof. In other embodiments, the treatment and inhibition of hepato-fibrotic conditions caused by contact with hepatotoxic chemical substances or by mechanical obstruction is contemplated.

14 Claims, 11 Drawing Sheets

Related U.S. Application Data filed on Nov. 10, 2016, provisional application No. 62/420,009, filed on Nov. 10, 2016.

(51) Int. Cl.

| | |
|---|---|
| *A61K 31/22* | (2006.01) |
| *A61K 31/727* | (2006.01) |
| *A61K 31/19* | (2006.01) |
| *A61K 31/397* | (2006.01) |
| *A61K 31/55* | (2006.01) |
| *A61K 31/575* | (2006.01) |
| *A61K 45/06* | (2006.01) |
| *A61P 1/16* | (2006.01) |
| *A61K 9/00* | (2006.01) |
| *A61P 19/04* | (2006.01) |
| *A61K 31/192* | (2006.01) |
| *A61K 31/715* | (2006.01) |
| *A61K 31/4439* | (2006.01) |

(52) U.S. Cl.
CPC .............. *A61P 1/16* (2018.01); *A61P 19/04* (2018.01); *A61K 31/192* (2013.01); *A61K 31/4439* (2013.01); *A61K 31/55* (2013.01); *A61K 31/715* (2013.01)

(58) Field of Classification Search
USPC ....................................................... 514/182
See application file for complete search history.

(56) References Cited

U.S. PATENT DOCUMENTS

| | | | |
|---|---|---|---|
| 6,562,829 B1 | 5/2003 | Pines et al. | |
| 6,589,946 B2 | 7/2003 | Gilat | |
| 7,501,403 B2 | 3/2009 | Gilat | |
| 8,110,564 B2 | 2/2012 | Gilat | |
| 8,729,046 B2 | 5/2014 | Rogler et al. | |
| 8,858,954 B2 | 10/2014 | Hsu et al. | |
| 8,975,246 B2 | 3/2015 | Gilat | |
| 9,498,484 B2 | 11/2016 | Fiorucci et al. | |
| 2011/0014126 A1 | 1/2011 | Evans et al. | |
| 2012/0157419 A1 | 6/2012 | Gilat et al. | |
| 2012/0214872 A1* | 8/2012 | Gilat | A61K 31/575 514/558 |
| 2012/0264824 A1* | 10/2012 | Mizuguchi | A61K 31/232 514/549 |
| 2014/0187633 A1 | 7/2014 | Manku et al. | |
| 2015/0359805 A1 | 12/2015 | Pellicciari et al. | |
| 2016/0023983 A1 | 1/2016 | Gagnon et al. | |
| 2016/0175223 A1 | 6/2016 | Dayan et al. | |
| 2016/0175324 A1 | 6/2016 | Dayan et al. | |
| 2016/0213639 A1 | 7/2016 | Suzuki et al. | |
| 2016/0154258 A1 | 9/2016 | Didsbury | |
| 2016/0304553 A1 | 10/2016 | Baharaff et al. | |
| 2017/0196891 A1 | 7/2017 | Halpern et al. | |
| 2019/0175619 A1 | 6/2019 | Hayardeny-Nissimov et al. | |

FOREIGN PATENT DOCUMENTS

| | | |
|---|---|---|
| WO | WO 1999/052932 | 10/1999 |
| WO | WO 2002/083147 | 10/2002 |
| WO | WO 2010/086864 | 8/2010 |
| WO | WO2014/093711 A1 | 6/2014 |
| WO | WO 2014/197738 | 12/2014 |
| WO | WO 2015/019358 | 2/2015 |
| WO | WO 2015/019359 | 2/2015 |
| WO | WO 2015/083164 | 6/2015 |
| WO | WO 2015/186126 | 12/2015 |
| WO | WO 2016/094570 | 7/2016 |
| WO | WO 2016/112305 | 7/2016 |
| WO | WO 2016/153948 | 9/2016 |
| WO | WO 2016/154258 | 9/2016 |
| WO | WO 2016/199137 | 12/2016 |
| WO | WO 2017-017677 | 2/2017 |
| WO | WO 2017-125929 | 7/2017 |
| WO | WO2017/210526 A1 | 7/2017 |
| WO | PCT/US2017/049869 | 9/2017 |

OTHER PUBLICATIONS

U.S. Appl. No. 15/789,564, filed Oct. 20, 2017, Hayardeny-Nissimov et al.
Bataller and Brenner (2005) "Liver fibrosis". The Journal of Clinical Investigation 115 (2) :209-18.
Civan (2016) "Hepatic Fibrosis", Merck Manuals Professional Edition, available online at: <http://www.merckmanuals.com/professional/hepatic-and-biliary-disorders/fibrosis-and-cirrhosis/hepatic-fibrosis.
Clinicaltrials.gov [Internet] "A Clinical Trial to Evaluate the Efficacy and Safety of Two Aramchol Doses Versus Placebo in Patient with NASH", National Library of Medicine NCT02279524, updated Oct. 30, 2014, available online at: <https://clinicaltrials.gov/archive/NCT02279524/2014_10_30>.
Clinicaltrials.gov [Internet] "A Clinical Trial to Evaluate the Efficacy and Safety of Two Aramchol Doses Versus Placebo in Patient with NASH", National Library of Medicine NCT02279524, updated Nov. 2, 2015, available online at: <https://clinicaltrials.gov/archive/NCT02279524/2015_11_02>.
Clinicaltrials.gov [Internet] "A Clinical Trial to Evaluate the Efficacy and Safety of Two Aramchol Doses Versus Placebo in Patient with NASH", National Library of Medicine NCT02279524, updated Feb. 8, 2017, available online at: <https://clinicaltrials.gov/archive/NCT02279524/2017_02_08>.
Friedman (2008) "Mechanism of Hepatic Fibrogenesis", Gastroenterology 134 ( 6) : 1655-69.
Galmed Pharmaceuticals Ltd. [INTERNET] "Aramchol Demonstrates Significant Anti-Fibrotic Effect in a Pre-clinical Model of Fatty Liver Disease", updated Mar. 30, 2016, available online at: <http://galmedpharma.investorroom.com/2 016-03-30-Aramchol-Demonstrates-Significant-Anti-Fibrotic-Effect-in-a-Pre-clinical-Model-of-Fatty-Liver-Disease>.
Gilat et al. (2002) "Dissolution of Cholesterol Gallstones in Mice by the Oral Administration of a Fatty Acid Bile Acid Conjugate", Hepatology 35: 597-600.
Gilat et al. (2003) "Prevention of Diet-Induced Fatty Liver in Experimental Animals By the Oral Administration of a Fatty Acid Bile Acid Conjugate (FABAC)", Hepatology 38(2) : 436-42.
Kleiner et al. (2005) "Design and Validation of a Histological Scoring System for Nonalcoholic Fatty Liver Disease", Hepatology 41 (6) :1313-21.
Mycriteria.com [Internet] "Histological Scoring System for Nonalcoholic Garry Liver Disease (NAFLD)", Components of NAFLD Activity Score (NAS) and Fibrosis Staging, updated May 11, 2007, available online at: <http://wwww.medicalcriteria.com/criteria/gas_nafld_print.htm>.
Nishida et al. (2013) "Spontaneous onset of nonalcoholic steatohepatitis and hepatocellular carcinoma in a mouse model of metabolic syndrome". Lab Invest 93 (2) :230-41.
Per Stal (2015) "Liver fibrosis in non-alcoholic fatty liver disease—diagnostic challenge with prognostic significance", World J Gastroenterol 21 (39) :11077-88.
Peverill et al. (2014) "Evolving Concepts in the Pathogenesis of NASH: Beyond Steatosis and Inflammation", Int. J. Mol. Sci. 15:8591-638.
Safadi et al. (2014) "The Fatty Acid-Bile Acid Conjugate Aramchol Reduces Liver Fat Content in Patients with Nonalcoholic Fatty Liver Disease", Clin Gastroenterol Hepatol. 12 (12) :2085-91.
Sanyal et al. (2015) "Challenges and Opportunities in Drug and Biomarker Development for Nonalcoholic Steatohepatitis: Findings and Recommendations From an American Association for the Study of Liver Diseases-U.S. Food and Drug Administration Joint Workshop", Hepatology 61 (4) :1392-405.
Singh et al. (2015) "Fibrosis Progression in Nonalcoholic Fatty Liver vs. Nonalcoholic Steatohepatitis", Clin Gastroenterol Hepetol 13 (4) :643-54.

(56) References Cited

OTHER PUBLICATIONS

S. Dept. Health and Human Svcs [Internet] Guidance for Industry In vivo drug metabolism/drug interaction studies—study design, data analysis, and recommendations for dosing and labeling, FDA, Ctr. for Drug Eval. and Res., Ctr. for Biologies Eval. and Res., Clin./Pharm., updated Nov. 1999, available online at: http://www.fda.gov/cber/gdlns/metabol.pdf.

Identifying Novel Targets for Treatment of Liver Fibrosis: What Can We Learn from Injured Tissues which Heal Without a Scar? Michele T. Pritchard et al.; Current Drug Targets. 2015 vol. 16, No. 12, 1332-1346.

Clinical advancements in the targeted therapies against liver fibrosis; Bansal et al—Mediators of inflammation, 2016—hindawi.com http://dx.doi.orq/10.1155/2016/7629724.

Fatty acid bile acid conjugate inhibits hepatic stearoyl coenzyme A desaturase and is non-atherogenic; Leikin-Frenkel et al.; Elsevier; Archives of medical research vol. 41, Issue 6, Aug. 2010, pp. 397-404 https://doi.org/10.1016/j.arcmed.2010.09.001.

Elafibranor, an Agonist of the Peroxisome Proliferator-Activated Receptor-α and -δ, Induces Resolution of Nonalcoholic Steatohepatitis Without Fibrosis Worsening; Ratziu et al: Gastroenterology: vol. 150, Issue 5, May 2016, pp. 1147-1159.e5.

Pioglitazone, Vitamin E, or Placebo for Nonalcoholic Steatohepatitis; Sanyal et al. ; N Engl J Med 2010; 362:1675-1685 May 6, 2010.

An overview of patented small molecule stearoyl coenzyme-A desaturase inhibitors (2009-2013); David A. Powell, PhD; pp. 155-175 Nov. 20, 2013; https://doi.org/10.1517/13543776.2014.851669.

Farnesoid X nuclear receptor ligand obeticholic acid for non-cirrhotic, non-alcoholic steatohepatitis (FLINT): a multicentre, randomised, placebo-controlled trial; Prof Brent A Neuschwander-Tetri MD et al.; The Lancet; vol. 385, Issue 9972, Mar. 14-20, 2015, pp. 956-965 https://doi.org/10.1016/SO140-6736(14)61933.4.

The ASK1 inhibitor seionsertib in patients with nonalcoholic steatohepatitis: A randomized, phase 2 trial; Loomba et al; Sep. 11, 2017; Hepatology; vol. 67 Iss.2 p. 549-559 https://doi.org/10.1002/hep.29514.

Role of Aramchol in steatohepatitis and fibrosis in mice; Marta Iruarrizaga-Lejarreta et al; Hepatology Communications; vol. 1 Iss. 9 Nov. 2017 p. 911-927 https ://doi.org/10.1002/hep4.1107.

Liver Fibrosis: Mechanisms of Development, Experimental Models and Treatment Strategies; Anumah et al; Research Journal of Pharmaceutical, Biological and Chemical Sciences 8(2):682-695 • Mar. 2017.

Molecular interplays in hepatic stellate cells: apoptosis, senescence, and phenotype reversion as cellular connections that modulate liver fibrosis; Brenda de Oliveira da Silva et ai; Cell Biology International; vol. 41. Iss 9; p. 946-959; Sep. 2017 ; https://doi-org/10.1002/cbin.10790.

A randomized, placebo-controlled trial of cenicriviroc for treatment of nonalcoholic steatohepatitis with fibrosis; Friedman et ai: Hepatology vol. 67 lss. 5 May 2018 p. 1754-1767 https://doi.org/10.1002/hep.29477.

Safadi, Rifaat, et al. "The Fatty Acid-Bile Acid Conjugate Aramchol Reduces Liver Fat Content In Patients With Nonalcoholic Fatty Liver Disease." Clinical Gastroenterology and Hepatology 12.12 (2014): 2085-2091.

Kurikawa, Nobuya, et al. "A novel inhibitor of stearoyl-CoA desaturase-1 attenuates hepatic lipid accumulation, liver injury and inflammation in model of nonalcoholic steatohepatitis." Biological and Pharmaceutical Bulletin 36.2 (2013): 259-267.

Eisenblaetter, T. et al (2018). Dose Linearity and Proportionality. In Drug discovery and Evalution: Methods in Clinical Pharmacology, Springer, Cham. P. Feb. 1-20, 2018.

Ratziu, Vlad, et al. "One-year results of the global phase 2b randomized placebo-controlled arrest trial of Aramchol, a stearoyl CoA desaturase inhibitor, in patients with NASH." Hepatology. vol. 68. No. 1. p. 1448A-1449A, Oct. 2018.

M. Iruarrizaga-Lejarreta et al; Role of Aramchol in Steatohepatitis and Fibrosis in Mice; Hepatology Communications, vol. 1, No. 9, Nov. 3, 2017 (Nov. 3, 2017) p. 911-927. XP002778683.

Trovato, Francesca Maria, et al. "4Ps medicine of the fatly liver: tne research model of predictive, preventive, personalized and participatory medicine—recommendations for facing obesity, fatty liver and fibrosis epidemics." *EPMA Journal* 5.1 (2014): 21.

Leikin-Frenkel, Alicia, et al. "Treatment of preestablished diet-induced fatty liver by oral fatty acid-bile acid conjugates in rodents." *European journal of gastroenterology & hepatology* 20.12 (2008): 1205-1213.

Aramchol demonstrates significant Anti-Fibrotic Effect in a Preclinical Model of Fatty Liver Disease; online Mar. 30, 2016, URL: https://galmedpharma.investorroom.com/2016-03-30-Aramchol-Demonstrates-Significant-Anti-Fibrotic-Effect-in-a-Pre-clinical-Model-of-Fatty-Liver-Disease.

Noureddin, Mazen, Alice Zhang, and Rohit Loomba. "Promising therapies for treatment of nonalcoholic steatohepatitis." Expert opinion on emerging drugs 21.3 (2016): 343-357.

Noureddin, M., Q. M. Anstee, and R. Loomba. "emerging antifibrotic therapies in the treatment of non-alcoholic steatohepatitis." *Alimentary pharmacology & therapeutics* 43.11 (2016): 1109-1123.

Brodosi, Lucia, et al. "NASH: A glance at the landscape of pharmacological treatment." *Annals of hepatology* 15.5 (2017): 673-681.

* cited by examiner

Normal Diet     0.1MCD Diet     0.1MCD Diet plus ARAMCHOL

Fig. 8A   Normal Diet        0.1MCD Diet        0.1MCD Diet plus ARAMCHOL™
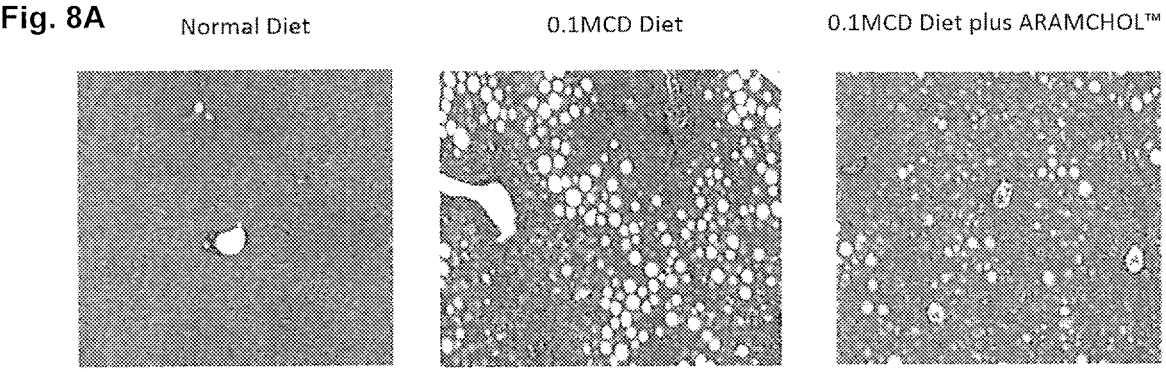
Fig. 8B
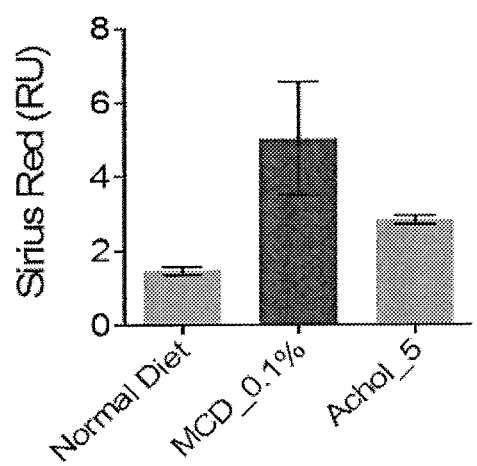

TREATMENT FOR HEPATIC FIBROSIS

This application claims the benefit of U.S. Provisional Application No. 62/475,129, filed Mar. 22, 2017, U.S. Provisional Application No. 62/420,017, filed Nov. 10, 2016, and U.S. Provisional Application No. 62/420,009, filed Nov. 10, 2016, the contents of each of which are hereby incorporated by reference.

Throughout this application various publications are referenced. The disclosures of these publications in their entireties are hereby incorporated by reference into this application in order to more fully describe the state of the art to which this invention pertains.

BACKGROUND OF THE INVENTION

Fibrosis

The formation of fibrous connective tissue is part of the normal healing process following tissue damage due to injury or inflammation. During this process, activated immune cells including macrophages stimulate the proliferation and activation of fibroblasts, which in turn deposit connective tissue. However, abnormal or excessive production of connective tissue may lead to accumulation of fibrous material such that it interferes with the normal function of the tissue. Fibrotic growth can proliferate and invade healthy surrounding tissue, even after the original injury heals. Such abnormal formation of excessive connective tissue, occurring in a reparative or reactive process, is referred to as fibrosis.

Fibrosis of the liver, also referred to herein as hepatic fibrosis, may be caused by various types of chronic liver injury, especially if an inflammatory component is involved. Self-limited, acute liver injury (e.g., acute viral hepatitis A), even when fulminant, does not necessarily distort the scaffolding architecture and hence does not typically cause fibrosis, despite loss of hepatocytes. However, factors such as chronic alcoholism, malnutrition, hemochromatosis, and exposure to poisons, toxins or drugs, may lead to chronic liver injury and hepatic fibrosis due to exposure to hepatotoxic chemical substances. Hepatic scarring, caused by surgery or other forms of injury associated with mechanical biliary obstruction, may also result in liver fibrosis.

Fibrosis itself is not necessarily symptomatic, however it can lead to the development of portal hypertension, in which scarring distorts blood flow through the liver, or cirrhosis, in which scarring results in disruption of normal hepatic architecture and liver dysfunction. The extent of each of these pathologies determines the clinical manifestation of hepatofibrotic disorders. For example, congenital hepatic fibrosis affects portal vein branches, largely sparing the parenchyma. The result is portal hypertension with sparing of hepatocellular function.

Treatment

In its initial stages, hepatic fibrosis may regress if the cause is reversible (e.g. with viral clearance). Thus, the majority of available treatment options are designed to remove the basis of the liver injury, such as by eliminating hepatitis B virus or hepatitis C virus in chronic viral hepatitis, abstaining from alcohol in alcoholic liver disease, removing heavy metals such as iron in hemochromatosis or copper in Wilson disease, and decompressing bile ducts in biliary obstruction.

Treatments aimed at reversing the fibrosis are usually too toxic for long-term use (e.g. corticosteroids, penicillamine) or have no proven efficacy (e.g. colchicine). Silymarin, present in milk thistle, is a popular alternative medicine used to treat hepatic fibrosis, appears to be safe but to lack efficacy.

Potential Therapeutic Agents

Attempts to develop specific anti-fibrotic agents for the treatment of liver diseases have been reported. For example, U.S. Pat. No. 8,729,046 relates to methods for treating fibrosis of a tissue, including fibrosis of the liver, using combinations of nucleic acids or nucleic acid analogs. Specifically, the nucleic acids or analogs thereof are targeted to microRNAs of the miR23b cluster. U.S. Pat. No. 6,562,829 discloses compositions for treating hepatic fibrosis and methods of using and manufacturing the composition, the composition comprising a quinazolinone derivative, preferably Halofuginone. U.S. Pat. No. 8,858,954 is directed to pharmaceutical composition for preventing and treating liver fibrosis or nonalcoholic fatty liver disease, comprising 50 to 90% by weight of *Cordyceps sinensis* mycelium powder, and 10 to 50% by weight of condensed *astragalus* powder.

U.S. Pub. No. 2015/359805 relates to Farnesoid X receptor (FXR) modulators which can be used for the treatment of cholestatic disorders, in particular to bile acid derivatives wherein the C6 contains an ethyl and the C24 carboxy group is transformed into a sulphate group. Among the disorders suggested to be treated are alcoholic liver disease, living donor transplant liver regeneration, congenital hepatic fibrosis, choledocholithiasis, and granulomatous liver disease. U.S. 2014/187633 is directed to methods of treating and/or preventing non-alcoholic seatohepatitis (NASH) and/or primary biliary cirrhosis comprising administering to a subject in need thereof a pharmaceutical composition comprising eicosapentaenoic acid or a derivative thereof. The FXR agonist, obeticholic acid, which is a modified bile acid, is in phase III clinical trials for primary biliary cirrhosis. Use of this drug has been reported to be commonly associated with side effects such as pruritus.

Ursodeoxycholic acid (UDCA, Ursodiol) is the most frequently used treatment for primary biliary cirrhosis. It is one of the secondary bile acids, which are metabolic byproducts of intestinal bacteria. The drug is considered to assist in reducing the cholestasis and improves blood test results (liver function tests). However it has a minimal effect on symptoms and whether it improves prognosis is controversial. To relieve itching caused by bile acids in circulation, which would normally be removed by the liver, cholestyramine (a bile acid sequestrant) may be prescribed to primary biliary cirrhosis patients. The agent may assist in absorbing bile acids in the gut to be eliminated, rather than re-enter the blood stream. Alternative agents include stanozolol, naltrexone and rifampicin.

Obeticholic acid (OCA, Ocaliva) is a semi-synthetic bile acid analogue undergoing development in phase 2 and 3 studies for specific liver and gastrointestinal conditions. The FDA granted accelerated approval to Ocaliva on 27 May 2016 for the treatment of primary biliary cholangitis (PBC) in combination with ursodeoxycholic acid (UDCA) in adults with an inadequate response to UDCA, or as a single therapy in adults unable to tolerate UDCA. In addition, a phase 2 trial in NASH patients showed that administration of OCA reduced markers of liver inflammation and fibrosis and increased insulin sensitivity.

WO 2014/197738 and WO 2016/094570 relate to small molecule compounds, disclosed to be inhibitors of myofibroblast trans-differentiation and activation. Drugs and combinations suggested for the treatment of inter alia fatty liver were disclosed, for example, in WO 2016/112305 and EP2632925 (acetyl-CoA carboxylase inhibitors) as well as WO 2016/154258 (dual PPAR delta/gamma agonists). Some of the disclosed compounds were suggested to be used in combination with various other drugs.

Many patients do not respond to available treatments for fibrotic disorders, and long term treatment is limited by toxicity and side effects. Therefore, a need remains for developing therapeutic modalities aimed at reducing fibrosis, especially hepatic fibrosis. The development of safe and effective treatments for established cirrhosis and portal hypertension and for attenuating fibrosis would be highly beneficial.

SUMMARY OF THE INVENTION

Fatty Acid Bile Acid Conjugates

Fatty acid bile salt conjugates, referred to also as Fatty Acid Bile Acid Conjugates (FABACs), are a family of synthetic molecules that may be used to improve conditions related to bile acids or cholesterol metabolism. FABACs are believed to lower blood cholesterol concentration, reduce liver fat levels and dissolve gallstones (Gilat et al., *Hepatology* 2003; 38: 436-442; and Gilat et al., *Hepatology* 2002; 35: 597-600). FABAC include 3β-arachidylamido-7α,12α-dihydroxy-5β-cholan-24-oic acid, also known as Aramchol.

U.S. Pat. Nos. 6,384,024, 6,395,722, 6,589,946 disclose certain FABACs and their use in dissolving cholesterol gallstones in bile and treating arteriosclerosis. These and additional FABACs were disclosed in U.S. Pat. Nos. 7,501,403, 8,975,246 and 8,110,564 for use in treating fatty liver, in reducing blood cholesterol levels and in treating hyperglycemia, diabetes, insulin resistance and obesity. Further therapeutic uses of FABACs are disclosed in Safadi et al. (Clin Gastroenterol Hepatol. 2014 December; 12(12):2085-91) and in WO 2015/019358 and WO 2015/019359. Amine salts of certain FABACs are disclosed in WO 2015/083164.

The invention relates to the treatment and reduction of fibrosis, specifically hepatic fibrosis. More specifically, embodiments of the invention provide compositions and methods useful for the treatment and inhibition of hepato-fibrotic conditions associated with Non-Alcoholic Fatty Liver Disease (NAFLD) and Non-Alcoholic Steatohepatitis (NASH), employing the use of 3β-arachidylamido-7α,12α-dihydroxy-5β-cholan-24-oic acid (Aramchol) or a pharmaceutically acceptable salt thereof. In other embodiments, the treatment and inhibition of hepato-fibrotic conditions caused by contact with hepatotoxic chemical substances or by mechanical obstruction is contemplated.

The invention provides Aramchol and medicaments comprising Aramchol for use in any of the methods of the invention.

Other objects, features and advantages of the present invention will become clear from the following description and drawings.

BRIEF DESCRIPTION OF THE DRAWINGS

FIG. 1. demonstrates the effect of Aramchol on liver cirrhosis by macroscopic evaluation.

FIG. 2. demonstrates the effect of Aramchol on liver fibrosis by microscopic evaluation (following Masson Goldner staining).

FIG. 6. depicts the effect of Aramchol on liver steatosis in 0.1 MCD diet.

FIG. 8. depicts the effect of Aramchol on fibrosis in 0.1 MCD Diet (histology—sirius red). FIG. 8A—histology staining using sirius red; FIG. 8B—quantification of sirius red stained cells.

FIG. 10. depicts the effects of Aramchol on liver biochemistry in 0.1 MCD mice.

DETAILED DESCRIPTION OF THE INVENTION

Aramchol

Figure 1A:
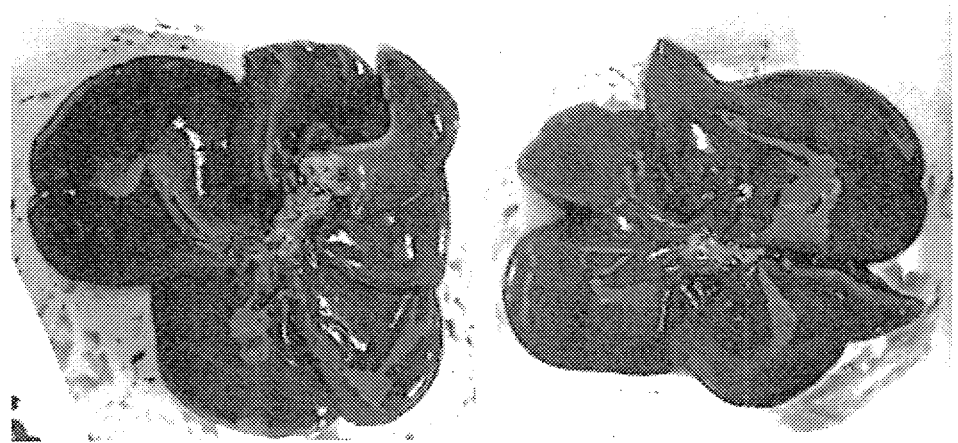
FIG. 1A—saline control.
Figure 1B:
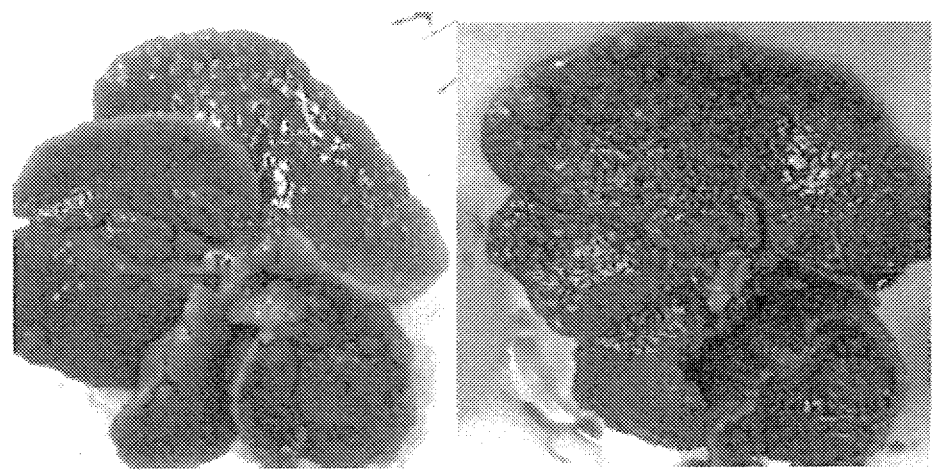
FIG. 1B—treatment with TAA (20 mg/100 gr body weight) twice per week during 10 weeks.
Figure 1C:
FIG. 1C—treatment with TAA and Aramchol 1 mg/kg.
Figure 1D:
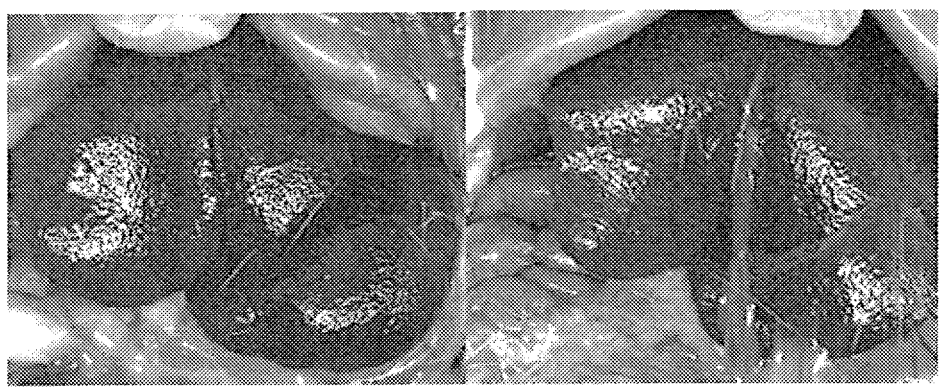
FIG. 1D—treatment with TAA and Aramchol 5 mg/kg.

Aramchol is chemically named 3β-arachidylamido-7α,12α-dihydroxy-5β-cholan-24-oic acid, and is represented by the following chemical structure:

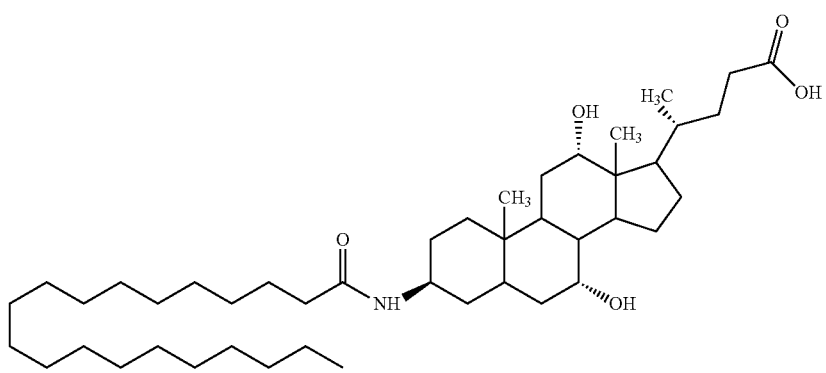 [SMILES: CCCCCCCCCCCCCCCCCCCC(=O)N[C@H]1CCC2(C)C(C1)C[C@@H](O)C1C2C[C@H](O)C2(C)C1CCC2[C@H](C)CCC(=O)O]

According to an embodiment of the invention, the combinations, compositions, methods and packages of the invention may comprise Aramchol in its free acid form. According to an embodiment of the invention, Aramchol is in its salt form. The salt may be an amine-based salt. The amine-based salt may be selected from the group consisting of meglumine, lysine and tromethamine salts.

Other embodiments of the invention relate to compositions, methods and packages employing the use of a Fatty Acid Bile Acid Conjugate (FABAC), or salts thereof. According to some embodiments, the FABAC is of Formula I:

W-X-G    (I)

wherein G represents a bile acid or a bile salt radical thereof; W represents one or two fatty acid radicals having 6-22 carbon atoms; and X represents a bonding member selected from the group consisting of: a heteroatom, a direct C—C bond and a C═C bond. Each possibility represents a separate embodiment of the present invention.

According to some embodiments, the bonding member is selected from the group consisting of: NH, P, S, O and a direct C—C or C═C bond. Each possibility represents a separate embodiment of the present invention. According to some embodiments, the bonding member is NH.

According to some embodiments, each of said one or two fatty acid radicals is a radical of a fatty acid selected from the group consisting of: arachidylic acid, stearic acid, behenic acid, palmitic acid, arachidonic acid, eicosapentaenoic acid and oleic acid. Each possibility represents a separate embodiment of the present invention. According to some embodiments, said one or two fatty acid radicals are radicals of arachidylic acid. Each possibility represents a separate embodiment of the present invention.

According to some embodiments, W represents two fatty acid radicals, each independently comprises 6-22 carbon atoms; and wherein each of said fatty acid radicals is independently bound to a bonding member X selected from the group consisting of: a heteroatom, a direct C—C bond and a C═C bond. According to some embodiments, W represents a single fatty acid radical.

According to some embodiments, the bile acid is selected from the group consisting of: cholic acid, ursodeoxycholic acid, chenodeoxycholic acid, deoxycholic acid, lithocholic acid and derivatives thereof. Each possibility represents a separate embodiment of the present invention. In another embodiment the bile acid is cholic acid, chenodeoxycholic acid, or deoxycholic acid. In another embodiment the bile acid is other than ursodeoxycholic acid and lithocholic acid. According to some embodiments, the bile acid is cholic acid.

Indications.

The invention is based, in part, on the surprising discovery that Aramchol exerts a potent anti-fibrotic effect, independent of its reported activities on fatty liver and steatosis, and reduces fibrosis in various experimental models. Specifically, treatment with Aramchol (5 mg/kg) significantly inhibited the development of toxin-induced cirrhosis, necrosis and liver fibrosis in an in vivo thioacetamide (TAA) model. Aramchol was also found to be unexpectedly superior to obaticholic acid (OCA), which did not induce statistically significant reduction in these parameters under the tested experimental conditions. In addition, Aramchol significantly reduced COL1A1 expression in LX-2 human hepatic stellate cells via PPARγ up-regulation. Aramchol was surprisingly found to be effective in reversing established fibrosis, and in reducing the production of collagen specifically in stellate cells.

Thus, independently from its reported activities on liver metabolism in subjects with NAFLD, Aramchol is surprisingly found herein to be effective in the treatment of new patient populations and patient subpopulations, such as in the treatment of hepatic fibrosis in patients with NAFLD or NASH, treatment of hepatic fibrosis in patients with NAFLD or NASH and advanced fibrosis (i.e. stage 2 or stage 3 fibrosis), treatment of hepatic fibrosis in patient with NAFLD or NASH who have cirrhosis (i.e. stage 4 fibrosis), treatment of hepatic fibrosis caused by contact with drugs, toxins or surgery, and specifically in alleviating hepatic cirrhosis. The invention advantageously provides for the treatment of these new patient populations with enhanced efficacy and/or safety and minimized side effects.

This invention provides a method for treating hepatic fibrosis in a human subject afflicted with hepatic fibrosis comprising administering to the subject greater than 300 mg per day of 3β-arachidylamido-7α, 12α-dihydroxy-5β-cholan-24-oic acid (Aramchol), or a pharmaceutically acceptable salt thereof, thereby treating hepatic fibrosis in said subject. In an embodiment the human subject being treated is afflicted with Non-Alcoholic Fatty Liver Disease (NAFLD).

In an embodiment the human subject being treated is afflicted with Non-Alcoholic Steatohepatitis (NASH).

In an embodiment the human subject is afflicted with NAFLD but not afflicted with Non-Alcoholic Steatohepatitis (NASH). In an embodiment the human subject has a NAFLD Activity (NAS) Score of at least 4. In an embodiment the human subject has a NAFLD Activity (NAS) Score of at least 5, at least 6, or at least 7. In an embodiment the human subject has a ballooning score of at least 1, an inflammation score of at least 1, and a steatosis score of at least 1.

In an embodiment the human subject is afflicted with NAFLD but not afflicted with Non-Alcoholic Steatohepatitis (NASH).

In an embodiment the human subject is afflicted with Diabetes Mellitus type II or pre-diabetes. One of the following 3 criteria is needed for pre-Diabetes: Fasting Plasma Glucose >100 mg/dl (5.5 mmol/l) or 2hPG following 75 g OGTT >140 (7.8 mmol/l) mg/dl or HbA1c>5.7%. HbA1c can be repeated at Investigator's discretion.

In an embodiment the subject's hepatic fibrosis is stage 2, 3, or 4 fibrosis.

In an embodiment the subject's hepatic fibrosis is stage 1 fibrosis.

In an embodiment the subject's hepatic fibrosis is stage 1a, stage 1b, or stage 1c fibrosis.

In an embodiment the human subject has a diet that is high fat and high calorie. As used herein, a high fat, high calorie diet contains at least 4000 calories per day, of which approximately 50% comes from fat.

In an embodiment the human subject is resistant to lifestyle intervention.

In an embodiment the human subject is resistant to diet intervention.

The invention further relates to the treatment and reduction of fibrosis, specifically liver fibrosis. The invention provides compositions and methods useful for the treatment of hepatic cirrhosis, portal hypertension, and hepato-fibrotic conditions caused by contact with hepatotoxic chemical substances or by mechanical obstruction. Compositions and methods according to the invention employ the use of 3β-arachidylamido-7α,12α-dihydroxy-5β-cholan-24-oic acid (Aramchol) or a pharmaceutically acceptable salt thereof.

In one aspect, there is provided a method for the treatment of hepatic fibrosis in a subject in need thereof, the hepatic fibrosis being caused by contact with a hepatotoxic chemical substance or by mechanical obstruction, comprising administering to the subject an effective amount of Aramchol, or a pharmaceutically acceptable salt thereof, thereby treating hepatic fibrosis in said subject.

In another aspect there is provided a method for the treatment of hepatic fibrosis in a subject in need thereof, comprising administering to the subject an effective amount of Aramchol or a pharmaceutically acceptable salt thereof, with the proviso that the fibrosis is associated with a disorder other than non-alcoholic liver disease and non-alcoholic steatohepatitis.

In another aspect there is provided a method for treating or inhibiting a disorder selected from the group consisting of hepatic cirrhosis and portal hypertension in a subject in need thereof, comprising administering to the subject an effective amount of Aramchol or a pharmaceutically acceptable salt thereof.

In another aspect there is provided a method of treating or inhibiting a fibrotic disease or condition in a subject in need thereof, comprising administering to the subject an effective amount of Aramchol or a pharmaceutically acceptable salt thereof, thereby treating or inhibiting the disease or condition in the subject, wherein said disease or condition is selected from the group consisting of: alcoholic liver disease, viral hepatitis, parasitic hepatitis, drug-induced hepatitis, toxin-induced hepatitis, primary biliary cirrhosis and congenital hepatic fibrosis.

Known indications suggested for FABAC treatment include those disclosed in U.S. Pat. Nos. 6,384,024, 6,395,722, 6,589,946, 7,501,403, 8,110,564 and 8,975,246, as detailed herein, and are explicitly excluded in an embodiment. In some embodiments, the subject to be treated by the methods of the invention is not afflicted with an additional medical condition.

Further, according to an aspect of the present invention, there is provided a method for the treatment of hepatic fibrosis in a subject in need thereof, the hepatic fibrosis being caused by contact with a hepatotoxic chemical substance or by mechanical obstruction, comprising administering to the subject an effective amount of Aramchol or a pharmaceutically acceptable salt thereof, thereby treating hepatic fibrosis in said subject.

According to embodiments of the present invention, the hepatic fibrosis is caused by a factor selected from the group consisting of chronic alcoholism, malnutrition, hemochromatosis, passive congestion, exposure to poisons or toxins, exposure to drugs, immune reactions, genetically determined sensitivities to a certain substance and infections.

In other embodiments, the hepatic fibrosis is caused by a factor selected from the group consisting of viral hepatitis, syphilis and a parasitic infection. In a particular embodiment, said parasitic infection is selected from the group consisting of *Schistosomiasis mansoni* and *S. japonica*. In another particular embodiment, the viral hepatitis is associated with is chronic hepatitis C infection.

According to another embodiment of the present invention, there is provided a method for the treatment of hepatic fibrosis in a subject, comprising administering to the subject an effective amount of Aramchol or a pharmaceutically acceptable salt thereof, with the proviso that the fibrosis is associated with a disorder other than non-alcoholic liver disease and non-alcoholic steatohepatitis.

In an embodiment, the subject is not diagnosed with fatty liver. In certain embodiments, the fibrosis is associated with a disorder selected from the group consisting of autoimmune hepatitis, storage or metabolism hepatic disorders, congenital hepatic fibrosis, infection, primary biliary cirrhosis and primary sclerosing cholangitis. Each possibility represents a separate embodiment of the invention. In a particular embodiment, the fibrosis is associated with congenital hepatic fibrosis, a developmental disorder of the liver, marked by formation of irregular broad bands of fibrous tissue containing multiple cysts formed by disordered terminal bile ducts, resulting in vascular constriction and portal hypertension.

Non-limiting examples for diseases associated with storage or metabolism abnormalities that are characterized by hepatic fibrosis (storage or metabolism hepatic disorders) include al-Antitrypsin deficiency, copper storage diseases (e.g., Wilson disease), fructosemia, galactosemia, glycogen storage diseases (especially types III, IV, VI, IX, and X), iron-overload syndromes (hemochromatosis), lipid abnormalities (e.g., Gaucher disease), peroxisomal disorders (e.g., Zellweger syndrome), and tyrosinemia. Each possibility represents a separate embodiment of the invention.

Non-limiting examples for infections characterized by liver fibrosis include bacterial infections (e.g., brucellosis), parasitic infections (e.g., echinococcosis), and viral infections (e.g., viral hepatitis including, but not limited to chronic hepatitis B or C). Each possibility represents a separate embodiment of the invention. In a particular embodiment, the infection is chronic hepatitis C infection.

According to yet further embodiments, the fibrosis is associated with contact with a hepatotoxic chemical substance, including, but not limited to alcohol, amiodarone, chlorpromazine, isoniazid, methotrexate, methyldopa, oxyphenisatin, and tolbutamide. Each possibility represents a separate embodiment of the invention. In a particular embodiment, said substance is alcohol.

According to further embodiments, the fibrosis is associated with mechanical obstruction, e.g. scarring due to prior liver surgery.

In another embodiment the disorder is associated with COL1A1 and/or PPAR-γ dysregulation in hepatic stellate calls. In a particular embodiment, said disorder is associated with COL1A1 up-regulation and PPAR-γ down-regulation in hepatic stellate calls of said subject.

In another aspect, there is provided a method for treating or inhibiting a disorder selected from the group consisting of hepatic cirrhosis and portal hypertension in a subject in need thereof, comprising administering to the subject an effective amount of Aramchol or a pharmaceutically acceptable salt thereof.

In another embodiment, said fibrosis is manifested by portal hypertension and/or hepatic cirrhosis. In a particular embodiment, said fibrosis is manifested by hepatic cirrhosis.

In one embodiment, the disorder is hepatic cirrhosis. In another embodiment, said disorder is portal hypertension. According to some embodiments, the methods of the invention advantageously provide for treating an existing condition of hepatic cirrhosis and/or portal hypertension. Thus, according to some embodiments, the method comprises determining whether said subject is afflicted with of hepatic cirrhosis and/or portal hypertension, and administering said Aramchol or a pharmaceutically acceptable salt thereof to a subject afflicted with of hepatic cirrhosis and/or portal hypertension. According to other embodiments, said of hepatic cirrhosis and/or portal hypertension is associated with a disorder as described herein. Each possibility represents a separate embodiment of the invention.

In other embodiments, the method is used for inhibiting or preventing a symptom of hepatic cirrhosis and/or portal hypertension. According to various specific embodiments, the method is used for inhibiting or preventing a symptom of portal hypertension, including, but not limited to variceal bleeding, ascites, and portosystemic encephalopathy. In other particular embodiments, the method is used for inhibiting or preventing a symptom of hepatic cirrhosis, including, but not limited to hepatic insufficiency and fatal liver failure. Each possibility represents a separate embodiment of the invention.

In another aspect, the invention provides a method of treating or inhibiting a fibrotic disease or condition in a subject in need thereof, comprising administering to the subject an effective amount of Aramchol or a pharmaceutically acceptable salt thereof, thereby treating or inhibiting the disease or condition in the subject, wherein said disease or condition is selected from the group consisting of: alcoholic liver disease, viral hepatitis, parasitic hepatitis, drug-induced hepatitis, toxin-induced hepatitis, primary biliary cirrhosis and congenital hepatic fibrosis. In another embodiment, said disease or condition is selected from the group consisting of: alcoholic liver disease, parasitic hepatitis, drug-induced hepatitis, and toxin-induced hepatitis. Each possibility represents a separate embodiment of the invention. In another embodiment, said disease or condition is chronic.

Administration and Dosage Form

According to some embodiments, the compound to be administered (e.g. Aramchol) is in the form of a composition (referred to as the composition of the invention) comprising a therapeutically effective amount of at least one of said compound. As used herein, the term "effective amount" means an amount of compound that is capable of reducing and/or attenuating a disorder or symptom as described herein. The specific dose of a compound administered according to this invention will, of course, be determined by the particular circumstances surrounding the case including, for example, the compound administered, the route of administration, the physiological state of the subject, and the severity of the condition being treated.

This invention provides a medicament comprising greater than 300 mg of 3β-arachidylamido-7α, 12α-dihydroxy-5β-cholan-24-oic acid (Aramchol) for use in administration to a human subject, including any of the human subjects recited hereinabove.

In an embodiment the medicament comprises greater than 350 mg of Aramchol. In an embodiment the medicament comprises between 350 mg and 1200 mg of Aramchol. In an embodiment the medicament comprises 400 mg, 500 mg, 600 mg, 700 mg, 800 mg, 900 mg, 1000 mg, 1100 mg, or 1200 mg of Aramchol. In an embodiment the medicament comprises between 400 mg and 1100 mg, or between 500 mg and 1000 mg, or between 600 mg and 900 mg of Aramchol. In an embodiment the medicament comprises 400 mg or 600 mg of Aramchol.

In an embodiment the medicament is to be administered daily.

This invention also provides 3β-arachidylamido-7α, 12α-dihydroxy-5β-cholan-24-oic acid (Aramchol) for use in administration to a human subject at a daily dose of greater than 300 mg. In an embodiment the human subject is any of the human subjects recited hereinabove.

In an embodiment the daily dose of Aramchol is greater than 350 mg. In an embodiment the daily dose of Aramchol is between 350 mg and 1200 mg. In an embodiment the daily dose of Aramchol is 400 mg, 500 mg, 600 mg, 700 mg, 800 mg, 900 mg, 1000 mg, 1100 mg, or 1200 mg. In an embodiment the daily dose of Aramchol is between 400 mg and 1100 mg, or between 500 mg and 1000 mg, or between 600 mg and 900 mg. In an embodiment the daily dose of Aramchol is 400 mg or 600 mg per day.

Any suitable route may be used to administer the medicament or Aramchol of the invention to a subject.

According to some embodiments, suitable administration routes may be systemic routes. According to some embodiments, administering is administering systemically. According to some embodiments, the composition is formulated for systemic administration.

According to another embodiment, administration systemically is through an enteral route. According to another embodiment, administration through an enteral route is oral administration. According to some embodiments, the composition is formulated for oral administration.

Thus, the inventions provides a method for treating the subjects recited in this application by administering Aramchol to the subject, wherein at least 350 mg of Aramchol is administered to the subject per day. In an embodiment between 350 mg and 1200 mg of Aramchol is administered to the subject per day. In an embodiment 400 mg, 500 mg, 600 mg, 700 mg, 800 mg, 900 mg, 1000 mg, 1100 mg, or 1200 mg of Aramchol is administered to the subject per day. In an embodiment between 400 mg and 1100 mg, or between 500 mg and 1000 mg, or between 600 mg and 900 mg of Aramchol is administered to the subject per day. In an embodiment 400 mg or 600 mg of Aramchol is administered to the subject per day.

In an embodiment the medicament or Aramchol is administered in the morning, in the afternoon, or in the evening.

In an embodiment the medicament or Aramchol is administered at the same time as, or within 30 minutes of a meal In an embodiment the meal is breakfast, lunch, or dinner.

In an embodiment the meal is a high fat meal. A high fat meal is a meal wherein approximately 500 to 600 calories are fat calories.

In an embodiment the meal is a high calorie meal. A high calorie meal is a meal of approximately 800 to 1000 calories.

In an embodiment the medicament or Aramchol is administered with water. In an embodiment the medicament or Aramchol is administered with at least 100 or at least 200 mL of water.

In an embodiment the Aramchol is administered over the course of at least 52 weeks, at least 72 weeks, at least 96 weeks, at least 2 years, at least 3 years, or at least 4 years.

According to some embodiments, oral administration is in the form of hard or soft gelatin capsules, pills, capsules, tablets, including coated tablets, dragees, elixirs, suspensions, liquids, gels, slurries or syrups and controlled release forms thereof. Thus the invention provides a method of administering Aramchol in the form of a tablet, a capsule, or in a liquid.

Suitable carriers for oral administration are well known in the art. Compositions for oral use can be made using a solid excipient, optionally grinding the resulting mixture, and processing the mixture of granules, after adding suitable auxiliaries as desired, to obtain tablets or dragee cores. Non-limiting examples of suitable excipients include fillers such as sugars, including lactose, sucrose, mannitol, or sorbitol, cellulose preparations such as, maize starch, wheat starch, rice starch, potato starch, gelatin, gum tragacanth, methyl cellulose, hydroxypropylmethyl-cellulose, and sodium carbomethylcellulose, and/or physiologically acceptable polymers such as polyvinylpyrrolidone (PVP).

If desired, disintegrating agents, such as cross-linked polyvinyl pyrrolidone, agar, or alginic acid or a salt thereof, such as sodium alginate, may be added. Capsules and cartridges of, for example, gelatin for use in a dispenser may be formulated containing a powder mix of the compound and a suitable powder base, such as lactose or starch.

Solid dosage forms for oral administration include without limitation capsules, tablets, pills, powders, and granules. In such solid dosage forms, the active compound is admixed with at least one inert pharmaceutically acceptable carrier such as sucrose, lactose, or starch. Such dosage forms can also comprise, as it normal practice, additional substances other than inert diluents, e.g., lubricating, agents. In the case of capsules, tablets and pills, the dosage forms may also comprise buffering agents. Tablets and pills can additionally be prepared with enteric coatings. The term "enteric coating", as used herein, refers to a coating which controls the location of composition absorption within the digestive system. Non-limiting examples for materials used for enteric coating are fatty acids, waxes, plant fibers or plastics.

Liquid dosage forms for oral administration may further contain adjuvants, such as wetting agents, emulsifying and suspending agents, and sweetening, flavoring and perfuming agents.

According to some embodiments, concomitant treatment with fatty acids such as ethyl eicosapentanoate, eicosapentaenoic acid, and their amides, salts and phospholipids is explicitly excluded. In other embodiment, concomitant treatment with bile acids such as ursodeoxycholic acid and lithocholic acid is excluded. In other embodiments concomitant treatment with vitamin D receptor agonists, acetyl-CoA carboxylase inhibitors, dual PPAR delta/gamma agonists, and inhibitors of myofibroblast trans-differentiation and activation is excluded. According to advantageous embodiments, Aramchol or the pharmaceutically acceptable salt thereof is used as a sole active ingredient.

According to some embodiments, the composition is administered in several dosages over prolonged periods until a sufficient response has been achieved.

As disclosed herein, Aramchol was found to be an unexpectedly potent therapeutic agent, capable of reversing established fibrosis and reducing cirrhosis and collagen synthesis in stellate calls even when used as a single therapeutic agent, in the absence of adjunct therapy. Thus, according to an advantageous embodiment of the methods of the invention, Aramchol or the pharmaceutically acceptable salt thereof is administered as a sole active ingredient. In another embodiment, the subject is human.

In another embodiment of the methods of the invention, Aramchol is administered orally. In another embodiment of the methods of the invention, Aramchol is in the form of Aramchol free acid. In another embodiment of the methods of the invention, Aramchol is in the form of an amine-based salt. In certain particular embodiments, the salt is a meglumine, lysine or tromethamine Aramchol salt. Each possibility represents a separate embodiment of the invention.

Patient Outcomes

In an embodiment treating the subject comprises lack of worsening of the subject's NAFLD Activity (NAS) score.

In an embodiment treating the subject comprises lack of worsening of the subject's Steatosis, Activity and Fibrosis (SAF) Activity score.

In an embodiment treating the subject comprises lack of worsening of the subject's fibrosis score.

In an embodiment the lack of worsening is lack of worsening at 52, 65, 72 or 96 weeks from the commencement of administration of Aramchol.

In an embodiment the lack of worsening is lack of worsening at 2, 3, or 4 years from the commencement of administration of Aramchol.

In an embodiment treating the subject treating comprises an improvement of the subject's NAFLD Activity (NAS) score.

In an embodiment the subject's NAS score is at least 4 at the commencement of administration of Aramchol and the improvement of the subject's NAS score is an improvement of at least 2 points.

In an embodiment treating the subject comprises an improvement of the subject's Steatosis, Activity and Fibrosis (SAF) Activity Score.

In an embodiment the subject's SAF Activity score is at least 4 at the commencement of administration of Aramchol and improvement of the subject's SAF Activity score is an improvement of at least 2 points.

In an embodiment treating the subject comprises an improvement of the subject's fibrosis score.

In an embodiment the improvement of the subject's fibrosis score is an improvement of 1 grade, or greater than 1 grade. In an embodiment improvement is improvement at 52, 65, 72, or 96 weeks from the commencement of administration of Aramchol.

In an embodiment improvement is improvement at 2, 3, or 4 years from the commencement of administration of Aramchol.

In an embodiment treating the subject comprises inhibiting progression of Non-Alcoholic Fatty Liver Disease (NAFLD).

In an embodiment inhibiting progression of NAFLD comprises prevention of progression, or reduced progression relative to a patient not treated with Aramchol.

In an embodiment the human subject is afflicted with Non-Alcoholic Steatohepatitis (NASH) and treating comprises inhibiting progression of NASH.

In an embodiment inhibiting progression of NASH comprises prevention of progression, or reduced progression relative to a patient not treated with Aramchol.

In an embodiment treating comprises preventing progression from Non-Alcoholic Fatty Liver Disease (NAFLD) to NASH.

In an embodiment improvement progression is progression at 2, 4, 8, 24, 40, 52, 65, 72, or 96 weeks from the commencement of administration of Aramchol.

In an embodiment improvement progression is progression at 2, 3, or 4 years from the commencement of administration of Aramchol.

In an embodiment the human subject is afflicted with Non-Alcoholic Steatohepatitis (NASH) and the treating comprises NASH resolution in the subject.

In an embodiment NASH resolution comprises the human subject having a ballooning score of 0 and an inflammation score of 0 or 1.

In an embodiment treating comprises NASH resolution in the subject at 52, 72, or 96 weeks from the commencement of administration of Aramchol.

In an embodiment treating comprises NASH resolution in the subject at 2, 3, or 4 years from the commencement of administration of Aramchol.

In an embodiment treating comprises a reduction in the level of liver triglycerides in the subject relative to the level at the commencement of administration of Aramchol.

In an embodiment treating comprises a reduction in the ratio of liver triglycerides to water in the subject relative to the ratio at the commencement of administration of Aramchol.

In an embodiment there is a greater than 10% reduction in ratio of liver triglycerides to water.

In an embodiment there is a 10% to 40% reduction in ratio of liver triglycerides to water.

In an embodiment there is a 15% to 35% reduction in ratio of liver triglycerides to water.

In an embodiment there is a 20% to 30% reduction in ratio of liver triglycerides to water.

In an embodiment treating comprises:
a. a reduction in the level of Hemoglobin A1C or HOMA-IR;
b. a reduction in the level of Fibrinogen, CK-18, C-reactive protein (CRP), TNFα, IL 6 and fibrosis Tests (NFS;
c. a reduction in the ratio of leptin to adinopectin; or
d. an increase in the level of adinopectin;
  in the subject relative to the level or ratio at the commencement of administration of Aramchol.

In an embodiment treating comprises:
a. a reduction in the human subject's body weight relative to the human subject's body weight at the commencement of administration of Aramchol;
b. a reduction in the human subject's waist circumference relative to the human subject's waist circumference at the commencement of administration of Aramchol; or
c. a reduction in the human subject's Fatty Liver Index relative to the human subject's Fatty Liver Index at the commencement of administration of Aramchol.

In an embodiment the reduction or increase is a reduction or increase at 2, 4, 8, 24, 40, 52, 65, 72, or 96 weeks from the commencement of administration of Aramchol.

In an embodiment the reduction or increase is a reduction or increase at 2, 3, or 4 years from the commencement of administration of Aramchol.

In another embodiment, administration of Aramchol or a pharmaceutically acceptable salt thereof according to the methods of the invention inhibits collagen synthesis (e.g. COL1A1 expression) in hepatic stellate calls. In another embodiment, administration of Aramchol or a pharmaceutically acceptable salt thereof according to the methods of the invention enhances PPAR-γ expression in hepatic stellate calls.

The present invention also provides a medicament or Aramchol of the invention wherein the medicament or Aramchol is effective to prevent worsening of NASH in the subject.

In an embodiment the medicament or Aramchol is effective to prevent worsening of fibrosis in the subject.

The present invention also provides a medicament or Aramchol of the invention wherein the human subject being administered the medicament or Aramchol is afflicted with fibrosis and wherein the medicament or Aramchol is effective to improve the human subject's fibrosis score.

In an embodiment the medicament or Aramchol is effective to improve the human subject's NAFLD Activity (NAS) score.

In an embodiment the medicament or Aramchol is effective to improve the human subject's NAFLD Activity (NAS) score by at least 2 points.

In an embodiment the medicament or Aramchol is effective to improve the human subject's Steatosis, Activity and Fibrosis (SAF) Activity score.

In an embodiment the medicament or Aramchol is effective to improve the human subject's Steatosis, Activity and Fibrosis (SAF) Activity score by at least 2 points.

In an embodiment the medicament or Aramchol is effective to resolve NASH in the human subject.

In an embodiment resolving NASH comprises reducing ballooning to a score of 0 and reducing inflammation to a score of 0 or 1.

In an embodiment the medicament or Aramchol is effective at 2, 4, 8, 24, 40, 52, 65, 72, or 96 weeks, or 2, 3, or 4 years from the commencement of administration.

In an embodiment the medicament or Aramchol is effective to reduce the level of liver triglycerides in the subject relative to the level at the commencement of administration.

In an embodiment the medicament or Aramchol is effective to reduce the ratio of liver triglycerides to water in the subject relative to the ratio at the commencement of administration.

In an embodiment the medicament or Aramchol is effective to reduce the ratio of liver triglycerides to water in the subject by at least 10% relative to the ratio at the commencement of administration.

In an embodiment the medicament or Aramchol is effective to reduce the ratio of liver triglycerides to water in the subject by between 10% and 40% relative to the ratio at the commencement of administration.

In an embodiment the medicament or Aramchol is effective to reduce the ratio of liver triglycerides to water in the subject by between 15% and 35% relative to the ratio at the commencement of administration.

In an embodiment the medicament or Aramchol is effective to reduce the ratio of liver triglycerides to water in the subject by between 20% and 30% relative to the ratio at the commencement of administration.

In an embodiment the medicament or Aramchol is effective to:
a. reduce the level of Hemoglobin A1C or HOMA-IR;
b. reduce the level of Fibrinogen, CK-18, C-reactive protein (CRP), TNFα, IL 6 and fibrosis Tests (NFS);
c. reduce the ratio of leptin to adinopectin; or
d. increase the level of adinopectin;
  in the subject relative to the level or ratio at the commencement of administration.

In an embodiment the medicament or Aramchol is effective to:
a. reduce the human subject's body weight relative to the human subject's body weight at the commencement of administration;
b. reduce the human subject's waist circumference relative to the human subject's waist circumference at the commencement of administration; or
c. reduce the human subject's Fatty Liver Index relative to the human subject's Fatty Liver Index at the commencement of administration.

In an embodiment the medicament or Aramchol is effective at 2, 4, 8, 24, 40, 52, 65, 72, or 96 weeks, or 2, 3, or 4 years from the commencement of administration.

Combination Therapy

The C—C motif chemokine receptor CCR5 is involved in the process by which HIV, the virus that causes AIDS, enters cells. CCR5 receptor antagonists are a class of small molecules that antagonize the CCR5 receptor. Hence, antagonists of this receptor are entry inhibitors and have potential therapeutic applications in the treatment of HIV infections. The C—C chemokine receptor type 2 (CCR2) is a protein that in humans is encoded by the CCR2 gene. This gene encodes two isoforms of a receptor for monocyte chemoattractant protein-1 (CCL2), a chemokine which specifically mediates chemotaxis of cells such as monocytes and macrophages. Cenicriviroc ((S,E)-8-(4-(2-Butoxyethoxy)phenyl)-1-isobutyl-N-(4-(((l-propyl-1H-imidazol-5-yl)methyl)

sulfinyl)phenyl)-1,2,3,4-tetrahydrobenzo[b]azocine-5-carboxamide, CAS No. 497223-25-3) is an inhibitor of both CCR2 and CCR5 receptors.

In an embodiment of the invention, the method further comprises administering a therapeutically effective amount of a pharmaceutical composition comprising a C—C chemokine receptor type 2 (CCR2) antagonist, a C—C chemokine receptor type 5 (CCR5) antagonist, a dual CCR2/CCR5 antagonist, or a combination or pharmaceutically acceptable salt thereof.

In an embodiment, the CCR2 antagonist is selected from the group consisting of: a double-stranded RNA, a compound antagonizing the binding of CCR2 to its ligand, a neutralizing antibody to CCR2, a ligand corresponding to a neutralizing antibody to CCR2, an isolated peptide derived from the sequences of CCR2 or analogs thereof capable of inhibiting CCR2, an antisense nucleic acid, an antagonist microRNA, and an enzymatic RNA molecule.

In an embodiment, the method further comprises administering to the subject a CCR5 antagonist and a CCR2 antagonist, or a dual CCR2/CCR5 antagonist.

In an embodiment, the CCR2/CCR5 dual antagonist is (S,E)-8-(4-(2-Butoxyethoxy)phenyl)-1-isobutyl-N-(4-(((1-propyl-1H-imidazol-5-yl)methyl)sulfinyl)phenyl)-1,2,3,4-tetrahydrobenzo[b]azocine-5-carboxamide (Cenicriviroc) or Cenicriviroc mesylate.

In an embodiment, the method comprises administering a daily dose of 50 to 500 mg of Cenicriviroc. In certain embodiments, the method described above comprises administering a daily dose of 10 to 200 mg of Cenicriviroc. In certain embodiments, the method comprises administering a daily dose of 50 to 500 mg, 50 to 400 mg, 50 to 300 mg, 50 to 200 mg, or 100 to 200 mg of Cenicriviroc. In certain embodiments, the method described above comprises administering a daily dose of 100-200 mg of Cenicriviroc. In an embodiment, the method comprises administering a daily dose of 100 or 200 mg of Cenicriviroc.

In some embodiments, the method further comprises administering a therapeutically effect amount of a pharmaceutical composition comprising at least one compound selected from the group consisting of ethyl eicosapentanoate (EPA-E), eicosapentaenoic acid (EPA) and its pharmaceutically acceptable amides, salts, esters and phospholipids.

In some embodiments, the EPA-E or EPA may be at least 40% by weight in total of the fatty acids and their derivatives.

In some embodiments, the pharmaceutical composition comprises Epadel® (Machida Pharmaceutical Co., Ltd., Tokyo Japan), Lovaza™ (GlaxoSmithKline, FL USA), Omacor™ (Pronova Biopharma ASA, Oslo Norway), Lotriga™ (Takeda Pharmaceutical Co., Ltd., Osaka Japan), Vascepa™ (Amarin Pharma Inc., NJ USA), Epanova™ (Astra Zeneca Pharmaceuticals LP, Wilmington, Germany) or Omtryg™ (Trygg Pharma Inc., VA USA).

Lovaza™, omega-3-acid ethyl esters, predominantly a combination of ethyl esters of eicosapentaenoic acid (EPA—approximately 465 mg) and docosahexaenoic acid (DHA—approximately 375 mg), is indicated as an adjunct to diet to reduce triglyceride (TG) levels in adult patients with severe (500 mg/dL) hypertriglyceridemia (Lovaza, Food and Drug Administration Approved Labeling (Reference ID:3371921) [online], GlaxoSmithKline, 2013).

The recommended dose and schedule for Lovaza™ is 4 g per day. The daily dose may be taken as a single 27 4-gram dose (4 capsules) or as two 2-gram doses (2 capsules given twice daily).

In some embodiments, the administration of Lovaza™ comprises 4.0 g per day, 3.5 g per day, 3.0 g per day, 2.5 g per day, 2.0 g per day, 1.5 g per day, 1.0 g per day or less of Lovaza™.

Omacor™, omega-3-acid ethyl esters, predominantly a combination of ethyl esters of eicosapentaenoic acid (EPA—approximately 465 mg) and docosahexaenoic acid (DHA—approximately 375 mg), is a a lipid-regulating agent. (Reference ID:"FPL for approved NDA 21-654") [online], Abbott Laboratories).

The recommended dose and schedule for Omacor™ is 4 g per day. The daily dose may be taken as a single 4-g dose (4 capsules) or as two 2-g doses (2 capsules given twice daily).

In some embodiments, the administration of Omacor™ comprises 4.0 g per day, 3.5 g per day, 3.0 g per day, 2.5 g per day, 2.0 g per day, 1.5 g per day, 1.0 g per day or less of Omacor™.

Vascepam, containing 1 gram of icosapent ethyl, an ethyl ester of the omega-3 fatty acid eicosapentaenoic acid (EPA), is a a lipid-regulating agent indicated as an adjunct to diet to reduce triglyceride (TG) levels in adult patients with severe 500 mg/dL) hypertriglyceridemia (Vascepam, Food and Drug Administration Approved Labeling (Reference ID:3783357) [online], Amarin Pharmaceuticals, 2012).

The recommended dose and schedule for Vascepa™ is 4 grams per day taken as 2 capsules twice daily with food.

In some embodiments, the administration of Vascepa™ comprises 4.0 g per day, 3.5 g per day, 3.0 g per day, 2.5 g per day, 2.0 g per day, 1.5 g per day, 1.0 g per day or less of Vascepa™.

Epanova™, containing 1 gram of fish oil-derived free fatty acids, designated "omega-3-carboxylic acids," with at least 850 mg of polyunsaturated fatty acids, including multiple omega-3 fatty acids (eicosapentaenoic acid [EPA] and docosahexaenoic acid [DHA] being the most abundant), is a lipid-regulating agent indicated as an adjunct to diet to reduce triglyceride (TG) levels in adult patients with severe (>500 mg/dL) hypertriglyceridemia (Epanova™, Food and Drug Administration Approved Labeling (Reference ID:3501113) [online], AstraZeneca Pharmaceuticals, 2014).

The recommended dose and schedule for Epanova™ is 4 grams per day taken as 2 grams (2 capsules) twice daily, or 4 grams (4 capsules) once daily.

In some embodiments, the administration of Epanova™ comprises 4.0 g per day, 3.5 g per day, 3.0 g per day, 2.5 g per day, 2.0 g per day, 1.5 g per day, 1.0 g per day or less of Epanova™.

Omtryg™, a combination of ethyl esters of omega-3 fatty acids predominantly a combination of ethyl esters of eicosapentaenoic acid (EPA—approximately 465 mg) and docosahexaenoic acid (DHA—approximately 375 mg), is a lipid-regulating agent, indicated as an adjunct to diet to reduce triglyceride (TG) levels in adult patients with severe (0.500 mg/dL) hypertriglyceridemia (Omtryg™, Food and Drug Administration Approved Labeling (Reference ID:3494935) [online], Trygg Pharma Inc., 2014).

The recommended dose and schedule for Omtryg™ is 4 grams per day taken as 2 grams (2 capsules) twice daily, or 4 grams (4 capsules) once daily.

In some embodiments, the administration of Omtryg™ comprises 4.0 g per day, 3.5 g per day, 3.0 g per day, 2.5 g per day, 2.0 g per day, 1.5 g per day, 1.0 g per day or less of Omtryg™.

The compositions recited hereinabove are described in U.S. Patent Application Publication No. 2016/0213639, the entire contents of which is incorporated by reference.

In some embodiments, the method further comprises administering a therapeutically effect amount of an inhibitor of Acetyl-CoA carboxylase (ACC) alone, or in combination with one or more additional therapeutic agents.

As used herein generally, "ACC inhibitor" means any therapeutic agent that reduces the activity of an acetyl CoA carboxylase enzyme.

Suitable ACC inhibitors include those described in WO2013/071169A1, WO2014/182943A1, WO2014/182945A1, WO2014/182950A1, and WO2014/182951A1, the entirety of each of which is hereby incorporated by reference.

In some embodiments, the ACC inhibitor is soraphen A.

In some embodiments, additional therapeutic agents are independently selected from the group consisting of angiotensin II receptor antagonists, angiotensin converting enzyme (ACE) inhibitors, caspase inhibitors, cathepsin B inhibitors, CCR2 chemokine antagonists, CCR5 chemokine antagonists, chloride channel stimulators, cholesterol solubilizers, diacylglycerol 0-acyltransferase 1 (DGATl) inhibitors, dipeptidyl peptidase IV (DPPIV) inhibitors, farnesoid X receptor (FXR) agonists, FXR/TGR5 dual agonists, galectin-3 inhibitors, glucagon-like peptide (GLPI) agonists, glutathione precursors, hepatitis C virus NS3 protease inhibitors, HMG CoA reductase inhibitors, I I ~-hydroxysteroid dehydrogenase (I I ~-HSD I) inhibitors, IL-I~ antagonists, IL-6 antagonists, IL-I 0 agonists, IL-I 7 antagonists, ileal sodium bile acid cotransporter inhibitors, leptin analogs, 5-lipoxygenase inhibitors, LPL gene stimulators, lysyl oxidase homolog 2 (LOXL2) inhibitors, PDE3 inhibitors, PDE4 inhibitors, phospholipase C (PLC) inhibitors, PPARa agonists, PPARy agonists, PPAR8 agonists, Rho associated protein kinase 2 (ROCK2) inhibitors, sodium glucose transporter-2 (SGLT2) inhibitors, stearoyl CoA desaturaseI inhibitors, thyroid hormone receptor~ agonists, tumor necrosis factor a (TNFa) ligand inhibitors, transglutaminase inhibitors, transglutaminase inhibitor precursors, PTPib inhibitors, and ASKI inhibitors.

The compositions recited hereinabove are described in PCT International Application Publication No. WO 2016/112305, the entire contents of which is incorporated by reference.

In some embodiments, the method further comprises administering a therapeutically effect amount of Pioglitazone hydrochloride (Actos®) or an enantiopure deuterium-enriched pioglitazone.

As used herein, the deuterated pioglitazone contains deuterium enrichment at the chiral center of pioglitazone and optionally in other locations in the compound. Further, the deuterium-enriched pioglitazone is provided in enantiomerically pure form.

In some embodiments, the deuterium-enriched compound having an optical purity of at least 75% enantiomeric excess.

Pioglitazone hydrochloride, the active ingredient of Actos®, is a thiazolidinedione and an agonist for peroxisome proliferatoractivated receptor (PPAR) gamma indicated as an adjunct to diet and exercise to improve glycemic control in adults with type 2 diabetes mellitus in multiple clinical settings (Actos®, Food and Drug Administration Approved Labeling (Reference ID:2983732) [online], Takeda Pharmaceuticals, 2009-2011).

The recommended dose and schedule for Actos® is 15 mg or 30 mg once daily starting dose. If there is inadequate glycemic control, the dose can be increased in 15 mg increments up to a maximum of 45 mg once daily.

In some embodiments, the administration of Actos® comprises 15 mg, 16 mg, 17 mg, 18 mg, 19 mg, 20 mg, 25 mg, 30 mg, 35 mg, 40 mg, or 45 mg or less of Actos®.

The compositions recited hereinabove are described in PCT International Application Publication No. WO 2016/153948, the entire contents of which is incorporated by reference.

In some embodiments, the method further comprises administering a therapeutically effect amount of a peroxisome proliferator activated receptor (PPAR) delta and gamma dual agonist.

In some embodiments, the delta activity is greater than gamma activity, and gamma activity is greater than alpha activity.

In some embodiments, the method further comprises administering a therapeutically effect amount of an indane acetic acids and their derivatives, which are dual PPAR delta and gamma agonists.

Exemplary additional therapeutic agents may include, but are not limited to combination with: farnesoid X receptor agonists such as obeticholic acid and Px-104, GR-MD-02, cysteamine bitartrate, simtuzumab, emricasan, GFT-505, CER-002, KD3010, KD3020, MBX8025, LUM002, RP-103, galectin-3 blockers such as LIPC-1010 and GR-MD-02, cenicriviroc, vascular adhesion protein-1 inhibitors such as PXS4728A, metformin, PPAR gamma agonists such as rosiglitazone and pioglitazone, metformin, pentoxyfylline, vitamin E, selenium, omega-3 fatty acids and betaine.

The compositions recited hereinabove are described in PCT International Application Publication No. WO 2016/154258, the entire contents of which is incorporated by reference.

The embodiments referred to above refer to several drugs being substantially effective in the body at a same time. Several drugs can be administered substantially at the same time, or can be administered at different times but have effect on the body at the same time. For example, this includes administering Aramchol before or subsequently, while functioning of Aramchol in the body is substantially extant.

Thus in some embodiments, the method further comprises administering a therapeutically effect amount of a pharmaceutical composition comprising at least one compound selected from the group consisting of:

ethyl eicosapentanoate (EPA-E), eicosapentaenoic acid (EPA) and its pharmaceutically acceptable amides, salts, esters and phospholipids;

an inhibitor of Acetyl-CoA carboxylase (ACC) alone, or in combination with one or more additional therapeutic agents;

pioglitazone hydrochloride or an enantiopure deuterium-enriched pioglitazone; and a peroxisome proliferator activated receptor (PPAR) delta and gamma dual agonist.

In some embodiments, additional therapeutic agents are independently selected from the group consisting of angiotensin II receptor antagonists, angiotensin converting enzyme (ACE) inhibitors, caspase inhibitors, cathepsin B inhibitors, CCR2 chemokine antagonists, CCR5 chemokine antagonists, chloride channel stimulators, cholesterol solubilizers, diacylglycerol 0-acyltransferase 1 (DGAT1) inhibitors, dipeptidyl peptidase IV (DPPIV) inhibitors, farnesoid X receptor (FXR) agonists such as obeticholic acid and Px-104, FXR/TGR5 dual agonists, galectin-3 inhibitors such as LIPC-1010 and GR-MD-02, glucagon-like peptide (GLPI) agonists, glutathione precursors, hepatitis C virus NS3 protease inhibitors, HMG CoA reductase inhibitors, I I ~-hydroxysteroid dehydrogenase (I I ~-HSD I) inhibitors, IL-I~ antagonists, IL-6 antagonists, IL-I 0 agonists, IL-I 7 antagonists, ileal sodium bile acid cotransporter inhibitors, leptin analogs, 5-lipoxygenase inhibitors, LPL gene stimulators, lysyl oxidase homolog 2 (LOXL2) inhibitors, PDE3 inhibitors, PDE4 inhibitors, phospholipase C (PLC) inhibitors, PPARa agonists, PPAR gamma agonists such as rosiglitazone and pioglitazone, metformin, pentoxyfylline, vitamin E, selenium, omega-3 fatty acids and betaine, PPAR8 agonists, Rho associated protein kinase 2 (ROCK2) inhibitors, sodium glucose transporter-2 (SGLT2) inhibitors, stearoyl CoA desaturaseI inhibitors, thyroid hormone receptor-agonists, tumor necrosis factor a (TNFa) ligand inhibitors, transglutaminase inhibitors, transglutaminase inhibitor precursors, PTPib inhibitors, ASKI inhibitors, and vascular adhesion protein-1 inhibitors such as PXS4728A, metformin, GR-MD-02, cysteamine bitartrate, simtuzumab, emricasan, GFT-505, CER-002, KD3010, KD3020, MBX8025, LUM002, RP-103, and cenicriviroc.

The administration of two drugs to treat a given condition, such as non-alcoholic fatty liver disease (NAFLD), raises a number of potential problems. In vivo interactions between two drugs are complex. The effects of any single drug are related to its absorption, distribution, and elimination. When two drugs are introduced into the body, each drug can affect the absorption, distribution, and elimination of the other and hence, alter the effects of the other. For instance, one drug may inhibit, activate or induce the production of enzymes involved in a metabolic route of elimination of the other drug. (Guidance for Industry, 1999) Thus, when two drugs are administered to treat the same condition, it is unpredictable whether each will complement, have no effect on, or interfere with the therapeutic activity of the other in a human subject.

Not only may the interaction between two drugs affect the intended therapeutic activity of each drug, but the interaction may increase the levels of toxic metabolites (Guidance for Industry, 1999). The interaction may also heighten or lessen the side effects of each drug. Hence, upon administration of two drugs to treat a disease, it is unpredictable what change will occur in the negative side effect profile of each drug.

Additionally, it is difficult to accurately predict when the effects of the interaction between the two drugs will become manifest. For example, metabolic interactions between drugs may become apparent upon the initial administration of the second drug, after the two have reached a steady-state concentration or upon discontinuation of one of the drugs. (Guidance for Industry, 1999)

It is understood that where a parameter range is provided, all integers within that range, and tenths thereof, are also provided by the invention. For example, "0.2-5 mg/kg/day" is a disclosure of 0.2 mg/kg/day, 0.3 mg/kg/day, 0.4 mg/kg/day, 0.5 mg/kg/day, 0.6 mg/kg/day etc. up to 5.0 mg/kg/day.

Each embodiment disclosed herein is contemplated as being applicable to each of the other disclosed embodiments. Thus, all combinations of the various elements described herein are within the scope of the invention.

The following examples are presented in order to more fully illustrate some embodiments of the invention. They should, in no way be construed, however, as limiting the broad scope of the invention.

EXAMPLES

Examples are provided below to facilitate a more complete understanding of the invention. The following examples illustrate the exemplary modes of making and practicing the invention. However, the scope of the invention is not limited to specific embodiments disclosed in these Examples, which are for purposes of illustration only.

Example 1—Thioacetamide (TAA)-Induced Fibrosis—Model for Hepatic Cirrhosis

Liver fibrosis was induced in Wistar rats by intraperitoneal injections of TAA (20 mg/100 gr body weight) twice per week during 10 weeks. I.p. application of TAA results in hepatic centrolobular necrosis, elevated transaminase activity and robust liver fibrosis. Treatment groups further included co-administration of Aramchol (1 or 5 mg/kg orally) or obaticholic acid (OCA, 5 mg/kg). A control group of saline-treated rats (in the absence of TAA administration) was further included. Rats were then sacrificed, and livers were observed macroscopically for signs of cirrhosis and necrotic lesions, and microscopically, following Masson Goldner staining. The fibrosis score, calculated at a scale of 0-4, was determined for each sample, wherein 0 indicates no fibrosis and 4 indicates advanced fibrosis and cirrhosis.

Figure 2A:
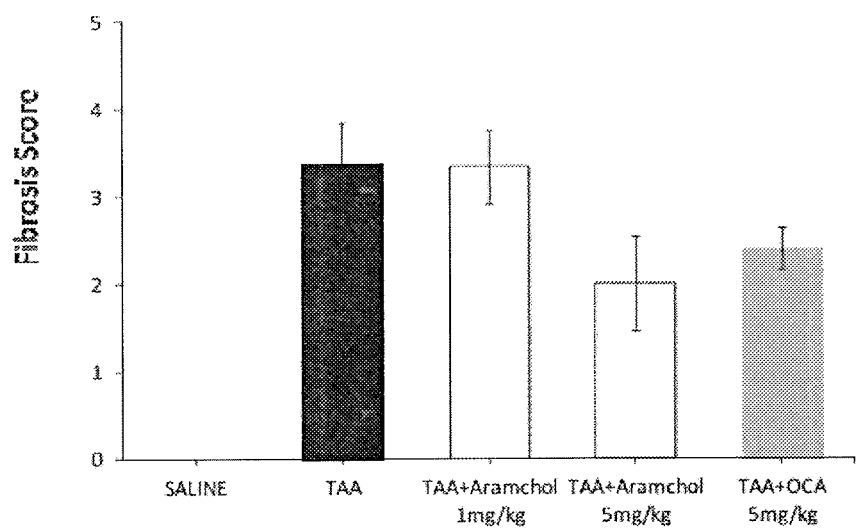
FIG. 2A—averaged fibrotic score (TAA—black, Aramchol—white, OCA—gray)
Figure 2B:
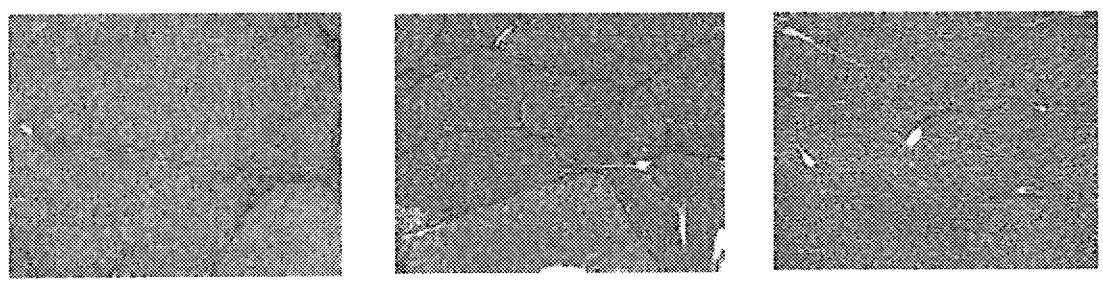
FIG. 2B—representative samples (TAA only—left; TAA and Aramchol 1 mg/kg—middle; TAA and Aramchol 5 mg/kg—right).

As can be seen in FIGS. 1-2, treatment with Aramchol (5 mg/kg) significantly prevented TAA induced fibrosis. The treatment reduced significantly the development of necrosis and cirrhosis (FIG. 1), as well as the fibrotic score and collagen distribution in the tissue (FIG. 2), in a dose-dependent manner. In contradistinction, OCA did not induce statistically significant reduction in these parameters.

Thus, Aramchol was surprisingly found to be a potent anti-fibrotic and anti-cirrhotic agent. Aramchol was also found to be unexpectedly superior to OCA and provide for improved, effective treatment for liver fibrosis.

Cirrhosis and portal hypertension from TAA intoxication may eventually lead to the development of acute liver failure and associated conditions such as hepatic encephalopathy, and the TAA model is also used in evaluating these phenomena. Accordingly, as disclosed herein, Aramchol may also be used in some embodiments for preventing acute or fatal liver failure and/or hepatic or portosystemic encephalopathy, for example toxin-induced liver failure and/or hepatic encephalopathy.

Example 2—Inhibition of Collagen Synthesis in Stellate Cells

LX2 cells (150.000 cells per well) were plated in DMEM media containing antibiotics, glutamine and bovine fetal serum. After 24 hours incubation, media was changed to 0% serum and incubated for an additional period of 16 hours. Then, Aramchol (10 mM) was added and 24 hours later RNA was extracted with Trizol.

Figure 3:
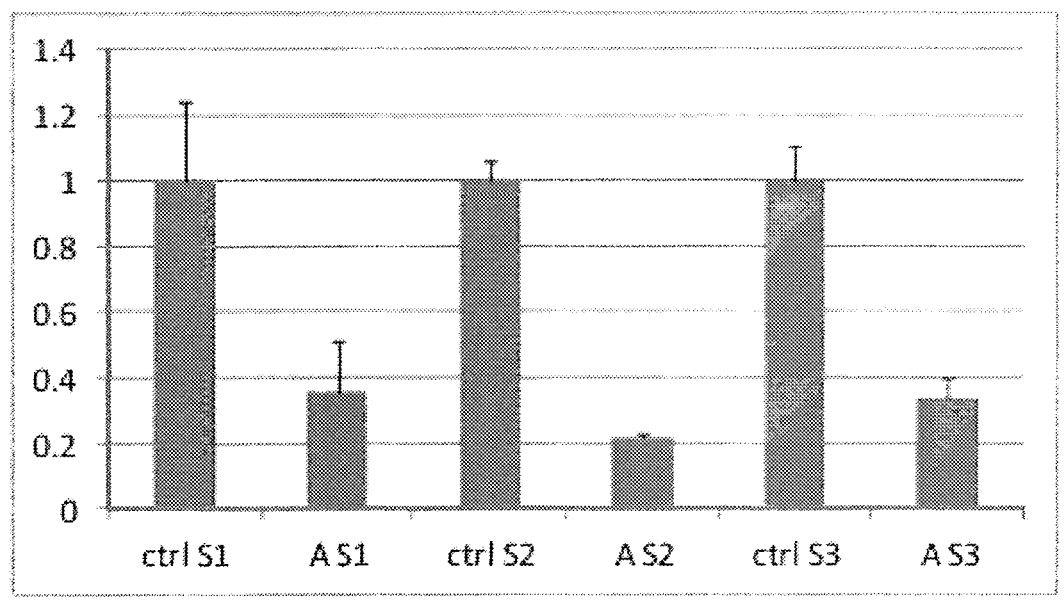
FIG. 3. depicts the effect of Aramchol on COL1A1 expression in LX-2 human hepatic stellate cells. "Ctrl S1, S2 and S3" represent control (saline-treated cells) in three separate experiments; "A S1, S2 and S3" represent the result of Aramchol treated cells in these experiments.
Figure 4:
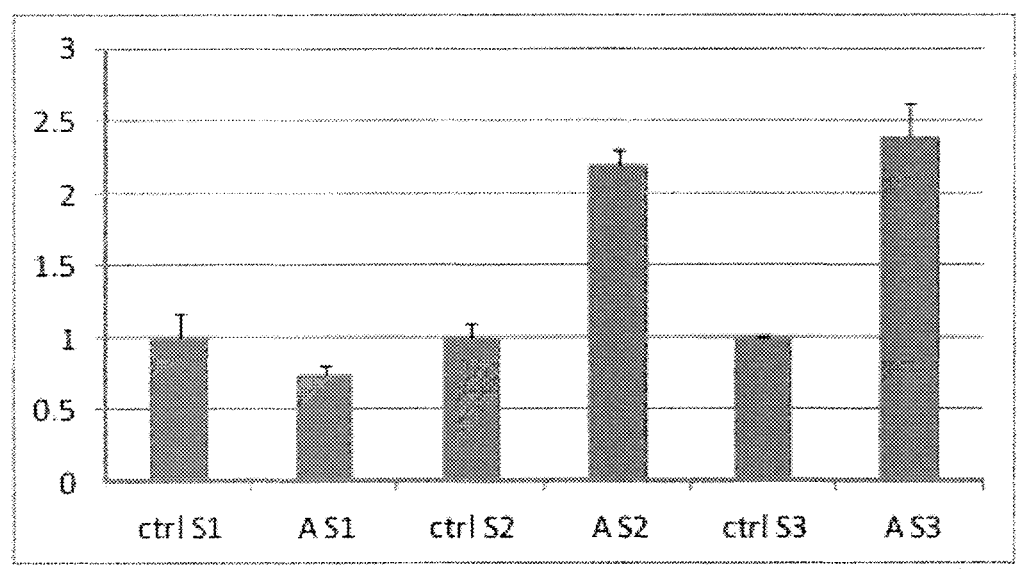
FIG. 4. depicts the effect of Aramchol on PPAR-γ expression in LX-2 human hepatic stellate cells. "Ctrl S1, S2 and S3" represent control (saline-treated cells) in three separate experiments; "A S1, S2 and S3" represent the result of Aramchol treated cells in these experiments.

Surprisingly, as can be seen in FIGS. 3 and 4, COL1A1 expression in LX-2 human hepatic stellate cells was reduced by Aramchol via PPARγ up-regulation.

Figure 5:
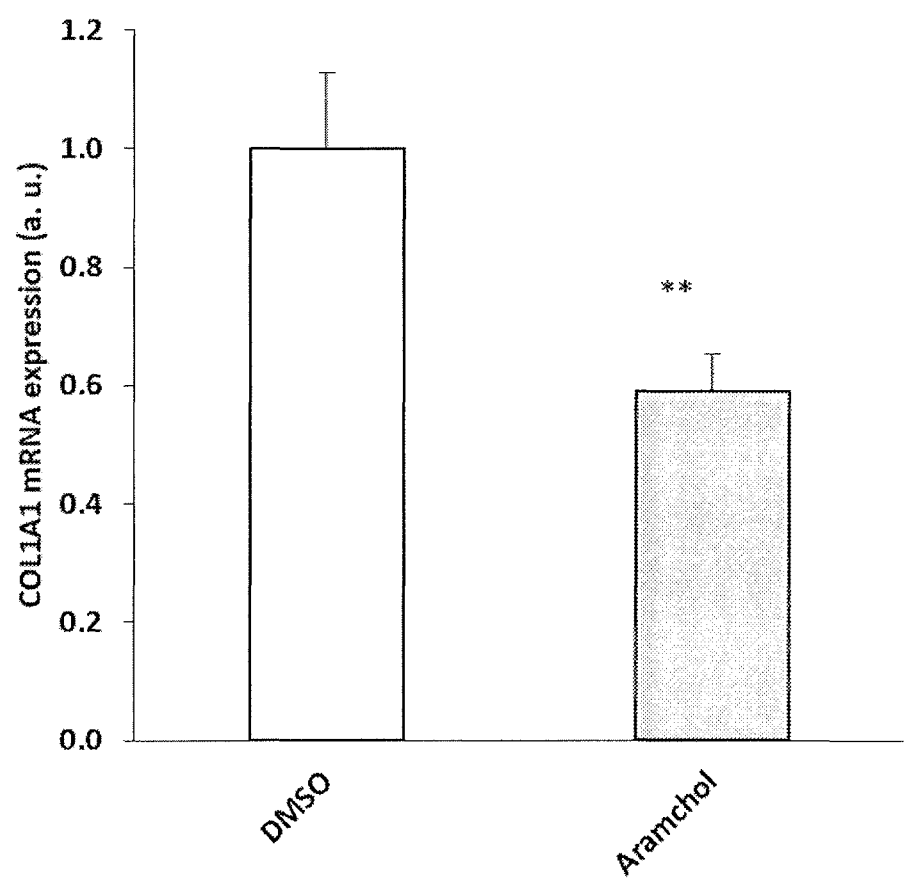
FIG. 5. depicts the effect of Aramchol on collagen production from LX-2 human hepatic stellate cells compared to a DMSO control.

Consistently, Aramchol significantly down regulates collagen production in LX-2 human hepatic stellate cells relative to a DMSO control (FIG. 5). Again, Aramchol was surprisingly found to be effective in reducing the production of collagen specifically in stellate cells.

Example 3—Aramchol Reduces Established Fibrosis in a MCD Diet Animal Model

The study described below investigates the mechanism of action of Aramchol and its potential effect on fibrosis using the 0.1% methionine- and choline-deficient (0.1 MCD) diet mouse model of NASH.

C57Bl/6 were fed the Methionine and Choline Deficient (MCD) and control diet and were sacrificed after 4 weeks. The MCD diet induces aminotransferase elevation and changes in hepatic histological features, characterized by steatosis, local inflammation, hepatocyte necrosis and fibrosis. These changes occur rapidly and are morphologically similar to those observed in human NASH. In this study the MCD diet contained 0.1% methionine to minimize and stabilize weight loss. At the end of the second week, after verification of established NASH, 0.1 MCD-fed mice were treated orally by gavage with Aramchol (5 mg/Kg/day) or vehicle (n=10, each condition). Control diet-fed mice were also treated with vehicle for same duration (n=10). At the end of the experiment, blood and liver samples were obtained.

Figure 6A:
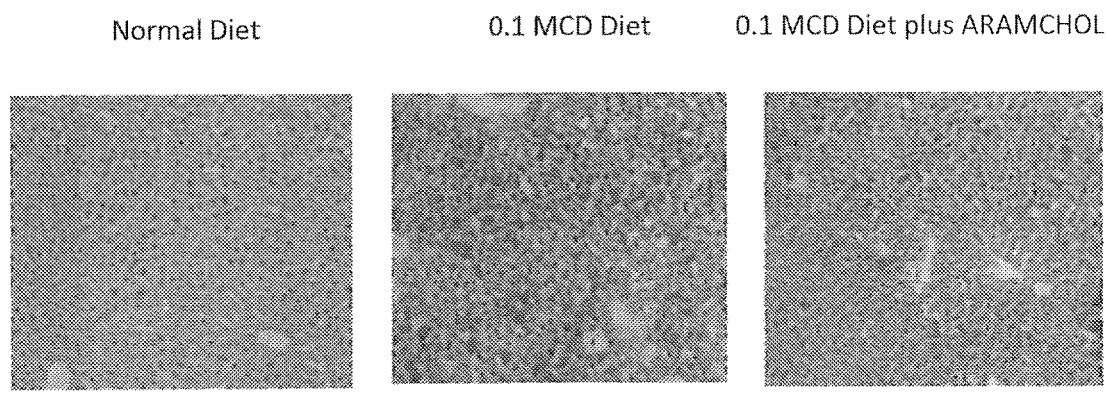
FIG. 6A—histology staining using Sudan III.
Figure 6B:
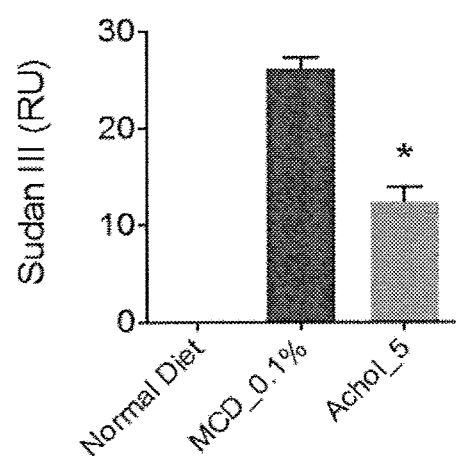
FIG. 6B—quantification of Sudan III stained cells.
Figure 7A:
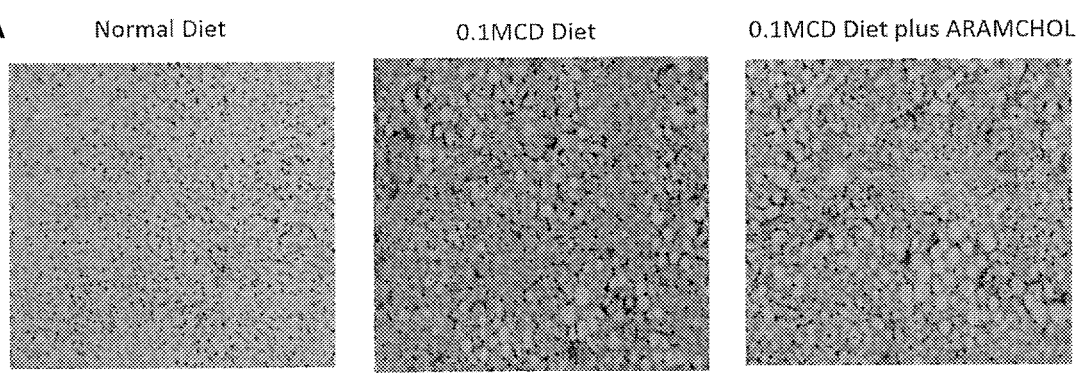
FIG. 7A—histology staining—F4/80 and CD64.
Figure 7B:
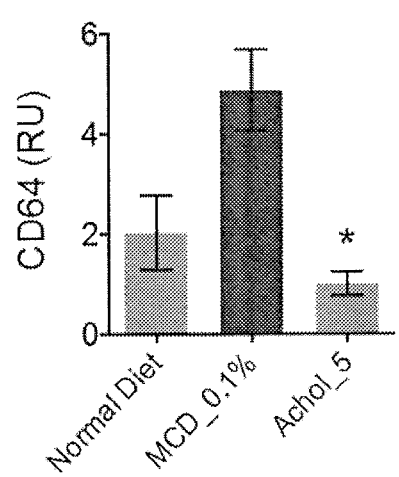
FIG. 7B—quantification of F4/80 and CD64 positive cells.
Figure 7C:
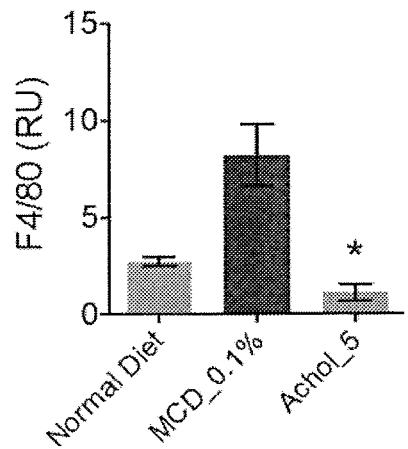
FIG. 7. depicts the effect of Aramchol on macrophage activation and infiltration in 0.1 MCD diet.
Figure 9:
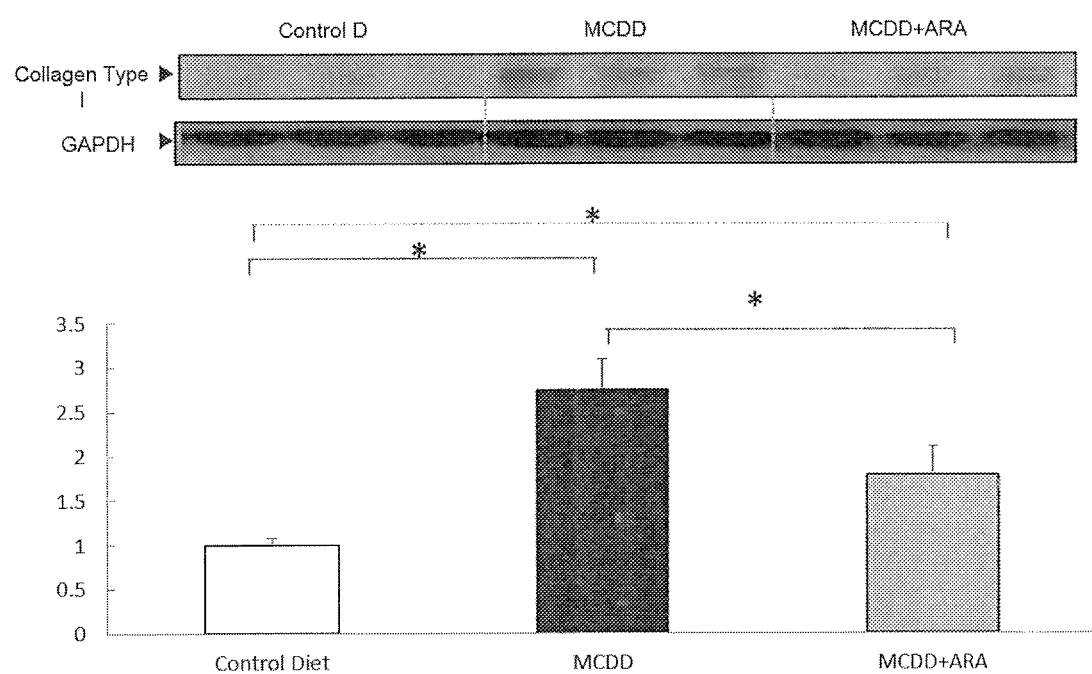
FIG. 9. depicts the effect of Aramchol on collagen production using liver extract from 0.1 MCD mice.
Figure 10A:
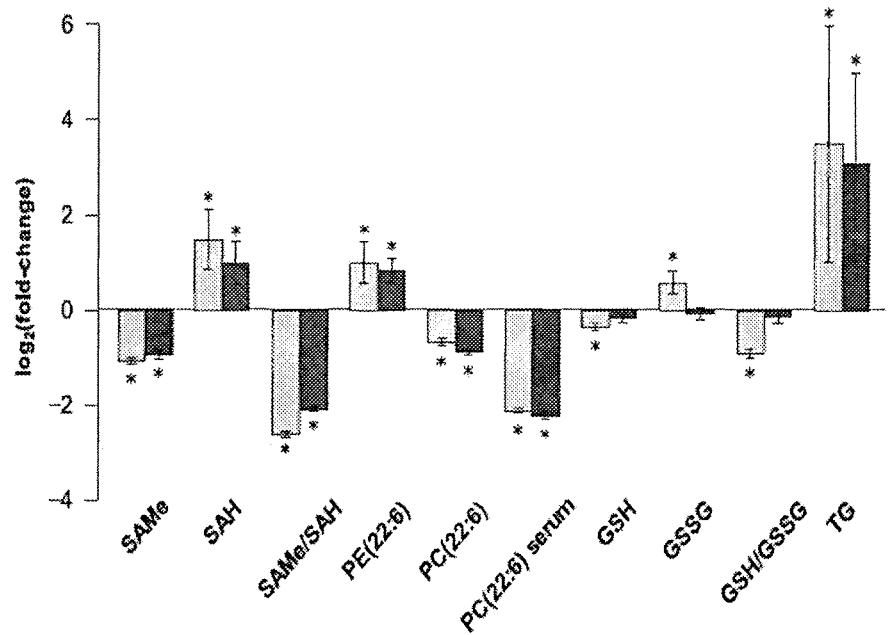
FIG. 10A—quantification of metabolites in liver of control (grey) and Aramchol-treated (black) 0.1 MCD mice.
Figure 10B:
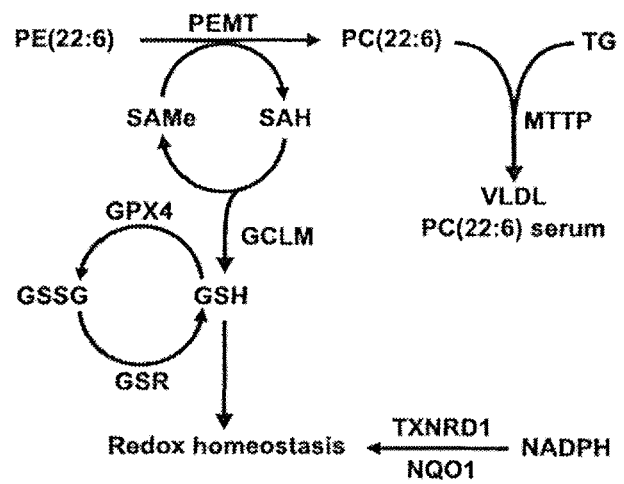
FIG. 10B—schematic of relevant liver biochemical pathway.

Results from the study showed: 1) treatment with Aramchol significantly down regulates steatosis in the liver (FIG. 6); 2) treatment with Aramchol significantly down regulates/normalizes infiltration and activation status of macrophages in the liver (FIG. 7); 3) treatment with Aramchol significantly down regulates/normalizes fibrosis in the liver (FIG. 8); 4) Aramchol significantly down regulates collagen in the liver (FIG. 9); and 5) Aramchol significantly up regulates glutathione and elevates GSH/GSSG ratio in 0.1% MCD mice (FIG. 10).

Additionally, Aramchol treatment further reduced SCD1 activity, which was evidenced by a marked decrease in SCD1 expression, in the FA(16:1)/FA(16:0) ratio and in the total content of monounsaturated FA (MUFA), which led to a reduction in the hepatic content of diglycerides (DG) and TG. Aramchol treatment improved oxidative stress, as shown by the normalization of the GSH/GSSG ratio, a biomarker of the cellular redox potential, and a marked reduction in the content of total oxFA including oxLA, which has been associated with liver injury in human NASH.

The foregoing description of the specific embodiments will so fully reveal the general nature of the invention that others can, by applying current knowledge, readily modify and/or adapt for various applications such specific embodiments without undue experimentation and without departing from the generic concept, and, therefore, such adaptations and modifications should and are intended to be comprehended within the meaning and range of equivalents of the disclosed embodiments. It is to be understood that the phraseology or terminology employed herein is for the purpose of description and not of limitation. The means, materials, and steps for carrying out various disclosed functions may take a variety of alternative forms without departing from the invention.

Example 4

Brief Summary

This is a multicenter, Phase IIb, randomized, double blind, placebo-controlled study designed to evaluate the efficacy and safety of two Aramchol doses in subjects that are 18 to 75 years of age, with Non-Alcoholic Steatohepatitis (NASH) confirmed by liver biopsy performed in a period of 6 months before entering the study, with overweight or obesity and who are pre diabetic or type II diabetic.

Intervention
  Drug: Aramchol
  Subjects will be administered Aramchol as follows:
    a. One tablet of Aramchol 400 mg and one tablet of matching placebo for Aramchol.
    b. One tablet of Aramchol 400 mg and one tablet of Aramchol 200 mg.
    c. Two tablet of Aramchol matching placebo. The tablets should be taken orally in the morning within 30 min after breakfast with a glass of water (250 ml).

Subjects are allowed to omit study drugs up to 3 consecutive days during the study.

Other Name: Placebo

Study Arms
  Experimental: Aramchol 600 mg
    a. One tablet of Aramchol 400 mg and one tablet of Aramchol 200 mg.
    b. Intervention: Drug: Aramchol
  Experimental: Aramchol 400 mg
    a. One tablet of Aramchol 400 mg and one tablet of matching placebo for Aramchol.
    b. Intervention: Drug: Aramchol
  Placebo Comparator: Placebo
    a. Two tablet of Aramchol matching placebo.
    b. Intervention: Drug: Aramchol Estimated Enrollment
  240

Inclusion Criteria
  Male or female age 18 to 75 years.
  BMI between 25 kg/m2 to 40 kg/m2 or waist circumference between 88 cm to 200 cm for women, and between 102 cm to 200 cm for men. If there is deviation above the upper limit, please consult the MRI center, to ensure that the machine is suitable for the patient.
  Known type II Diabetes Mellitus or pre-Diabetes according to American Diabetes Association. One of the following 3 criteria is needed for pre-Diabetes: Fasting Plasma Glucose >100 mg/dl (5.5 mmol/l) or 2hPG following 75 g OGTT >140 (7.8 mmol/l) mg/dl or HbA1c >5.7%. HbA1c can be repeated at Investigator's discretion.
  Histologically proven Steatohepatitis on a diagnostic liver biopsy performed either during screening or within 6 months before screening visit, confirmed by central laboratory reading of the slides. (Steatosis ≥1+inflammation ≥1+ballooning ≥1). Total activity NAS score of 4 or more.
  Liver fat concentration in the liver of 5.5% or more as measured by NMRS.
  Biopsies with an activity NAS score of 4 or more.
  Normal synthetic liver function (serum albumin >3.2 g/dl, INR 0.8-1.2, conjugated bilirubin <35 μmol/L).
  Understanding the nature of the study and signature of the written informed consent.
  Negative pregnancy test at study entry for females of child bearing potential.
  Females of child bearing potential practicing reliable contraception throughout the study period (including oral contraceptives) as well as negative pregnancy test at study entry.
  Hypertensive patients must be well controlled by stable dose of anti-hypertensive medication for at least 2 months prior to screening.
  Patients previously treated with vitamin E (>400 IU/day), Polyunsaturated fatty acid (>2 g/day) or Ursodeoxycholic acid or fish oil can be included if stopped or at least maintained on stable dose at least 3 months prior to diagnostic liver biopsy (and are not started during the trial). These treatments-dosages are allowed if they were stable for at least 12 months prior to biopsy and can remain stable throughout the study. (Dosages less than the amounts stated above are allowed without washout- or stable-period restrictions).

For patients with type II Diabetes, glycaemia must be controlled (Glycosylated Hemoglobin A1c ≤9%) while any HbA1c change should not exceed 1.5% during 6 months prior to enrolment). Treatments with anti-diabetic medications (except for those mentioned in Exclusion 16) are permitted if glycaemia is self-monitored by the patient. HbA1c can be repeated at Investigator's discretion.

Exclusion Criteria

Exclusion Criteria:

Patients with other active (acute or chronic) liver disease other than NASH (e.g. viral hepatitis, unless eradicated at least 3 years prior to screening; genetic hemochromatosis; Wilson disease; alpha lantitripsin deficiency; alcohol liver disease; drug-induced liver disease) at the time of randomization.

Patients with clinically or histologically documented liver cirrhosis

Known alcohol and/or any other drug abuse or dependence in the last five years.

Known history or presence of clinically significant cardiovascular, gastrointestinal, metabolic other than Diabetes Mellitus, neurologic, pulmonary, endocrine, psychiatric, neoplastic disorder or nephrotic syndrome, that in the opinion of the Investigator warrant exclusion from the study.

Patients with familial (i.e., genetic) hypertriglyceridemia and familial (i.e., genetic) hypercholesterolemia.

History or presence of any disease or condition known to interfere with the absorption distribution, metabolism or excretion of drugs including bile salt metabolites (e.g. inflammatory bowel disease (IBD)), previous intestinal (ileal or colonic) operation, chronic pancreatitis, celiac disease or previous vagotomy. Ongoing Chronic constipation Patients with heart or brain pacemaker (i.e., implantable neurological devices).

Surgery during the last three month before screening which involved stent implantation of metal devices (e.g. knee, hip etc.)

Weight loss of more than 5% within 6 months prior to randomization.

History of bariatric surgery within 5 years of liver biopsy.

Uncontrolled arterial hypertension.

Women who are pregnant and breast feeding.

Diabetes Mellitus other than type II (type I, endocrinopathy, genetic syndromes etc.).

Patients with HIV infection.

Daily alcohol intake >20 g/day for women and >30 g/day for men (on average per day) as per medical history.

Treatment with other anti-diabetic medications: GLP-1 receptor agonists and Thiazolidinediones (TZDs), unless started at least 12 months prior to biopsy and on stable dose for 6 months. In case of GLP-1 receptor agonists stopped, it should be at least 6 months before biopsy as per medical history.

SGLT-2 Inhibitors, Metformin, fibrates, statins, insulin, DPP-4 inhibitors and sulfonylurea unless prescribed dose has been stable for the last 6 months prior to the biopsy.

Treatment with Valproic acid, Tamoxifen, Methotrexate, Amiodarone or chronic treatment with anti-cholinergic agents, corticosteroids, high dose estrogen and tetracycline within 12 months prior to the screening visit.

Chronic treatment with antibiotics (e.g. Rifaximin).

Homeopathic and/or alternative treatments. Any treatment should be stopped during the screening period at least 48 hours before randomization.

Uncontrolled hypothyroidism defined as Thyroid Stimulating hormone >2× the upper limit of normal (ULN). Thyroid dysfunction controlled for at least 6 months prior to screening is permitted.

Patients with renal dysfunction eGFR<40.

Unexplained serum creatine phosphokinase (CPK) >3× the upper limit of normal (UNL). Patients with a reason for CPK elevation may have the measurement repeated prior to randomization; a CPK retest >3×ULN leads to exclusion.

Patients with condition(s) that makes them unsuitable to perform the NMRS (as determined by the PI or the MRI facility).

Hypersensitivity to Aramchol or to any of the excipients in the tablets

Hypersensitivity to cholic acid or bile acid sequestrants

DETAILED DESCRIPTION

This is a multicenter, Phase IIb, randomized, double blind, placebo-controlled study designed to evaluate the efficacy and safety of two Aramchol doses in subjects that are 18 to 75 years of age, with Non-Alcoholic Steatohepatitis (NASH) confirmed by liver biopsy performed in a period of 6 months before entering the study, with overweight or obesity and who are pre diabetic or type II diabetic.

Eligible subjects will be enrolled into three treatments arms: Aramchol 400 and 600 mg tablets and placebo tablets in ratio 2:2:1.

The subjects will be evaluated at study sites for 11 scheduled visits: at screening (visit 1 (weeks −4-0)), baseline (visit 2 (day 0)), visit 3 (week 2), visit 4 week 4), visit 5 (week 8), visit 6 (week 12), visit 7 (week 24), visit 8 (week 32), visit 9 (week 40) and visit (week 52−(End of Treatment/early termination visit)). After completion of the study treatment period, the subjects will be followed for an additional period of 13 weeks without study medication (until visit 11 (week 65)).

During the screening period, the severity of the disease will be evaluated with blood tests, liver biopsy and NMRS.

During the study the following assessments will be performed:

a. Vital signs will be measured at each study visit.
b. A physical examination will be performed at the screening visit, 24 weeks, End of Treatment/early termination and week 65 visit.

The following blood tests will be performed: complete blood count (CBC), serum chemistry (including electrolytes, liver enzymes, direct and total bilirubin, glucose, lipid profile which include triglyceride, cholesterol, HDL, LDL and VLDL, CPK, creatinine, urea, albumin, alkaline phosphatase), ESR and urinalysis during the screening visit, baseline, week 2, 4, 8, 24, 40, 52 and 65 (end of follow up) visits. Serology (HBV, HCV and HIV) will be performed during the screening visit. Coagulation (fibrinogen, PT/INR, aPTT) will be measured in screening and baseline, week 24, End of Treatment/early termination and week 65 visits. Insulin (HOMA) will be measured in the screening, week 24 and End of Treatment/early termination visits. HbA1C will be measured in the screening, week 8, 24, 40 and End of Treatment/early termination visits. C reactive protein, Leptin, Adiponectin, CK-18 (M30 and M65), Ferritin, PAI-1, IL-6, TNF-alpha, FGF-19, C4 (7-alpha-hydroxy-4-cholesten-3-one), pool serum Bile Acids, B-hydroxybutyrate and Free Fatty Acids will be measured in baseline visit and end of treatment period. The blood samples taken at these visits, will be tested for possible biomarkers, including, but not limited to, Fetuine A and GDF15. TSH, T3 and T4 will be measured during the screening visit. beta-hCG in women of childbearing potential will be performed during the screening visit. A serum sample will be collected and kept frozen until study end in case special investigation needs to be performed. This sample will be collected during the screening and visit 10/Early Termination.

Body weight and waist circumference will be measured in screening, baseline, week 24, end of treatment and week 65 visits. Height will be measured during the screening visit.

ECG will be performed during the screening visit, visit 7 (week 24) and end of treatment visits.

All subjects will undergo two NMRS scans, at screening and end of treatment visits.

FibroMax test will be performed only if the investigator thinks it is necessary

Liver biopsy will be conducted during the screening and end of treatment visit. The biopsy in the screening visit will be performed only if it was not done within the 6 months prior to this visit.

Metabolomics blood test will be performed at the screening, visit 7 and the End-of-Treatment/Early Termination visits. From some consenting patients (about 15) a sample from the liver biopsy will be taken for analysis.

Endothelial Function will be conducted in selected sites. The test will be conducted during the baseline visit before the study treatment will be given and End of Treatment/early termination visit.

Blood sample for Aramchol trough level will be collected (pre-dose) from patients in Israel at baseline (visit 2) week 4 (visit 4), week 12 (visit 6), week 24 (visit 7), week 40 (visit 9), end of treatment (visit 10) and follow up (visit 11). At selected sites in Mexico, USA and Hong Kong one blood sample will be collected (pre-dose) on visit 4 (up to 10 subjects per country) to test for trough Aramchol blood level differences between populations (e.g., African American, Asian, Hispanic).

Blood sample for gene analysis will be taken from all consenting patients during the baseline visit, will be kept frozen and analyzed only at the study end.

Life style questionnaire will be completed in all visits.

Adverse events will be monitored throughout the study.

Concomitant Medications will be monitored throughout the study.

Telephone contacts will be performed on week 16, 20, 28, 36, 44 and 48. An interim safety analysis will be conducted as soon as 120 subjects will completed the follow up period of 24 weeks under study treatment. An independent DSMB will analyze the safety data and recommend a continued course of action. All patients will continue to be treated under the study protocol until conclusion of the analysis will be known.

Safety assessment will include frequency and severity of treatment-emergent AEs, clinically significant laboratory abnormalities, ECG changes and physical examination findings.
Results
Primary and Secondary Outcome Measures (400 mg arm)

Treatment with 400 mg of Aramchol significantly reduces liver triglycerides ratio as measured by Magnetic Resonance Spectroscopy (MRS).

Treatment with 400 mg of Aramchol reduces liver triglycerides ratio as measured by Magnetic Resonance Spectroscopy (MRS) by 10-40%.

Treatment with 400 mg of Aramchol reduces liver triglycerides ratio as measured by Magnetic Resonance Spectroscopy (MRS) by 15%-35%.

Treatment with 400 mg of Aramchol reduces liver triglycerides ratio as measured by Magnetic Resonance Spectroscopy (MRS) by 20%-30%.

Treatment with 400 mg of Aramchol results in a significantly higher proportion of subjects having fibrosis improvement (i.e. decrease > or = to 1 point) without a worsening of NASH, compared to subjects treated with a placebo.

Treatment with 400 mg of Aramchol results in a significantly higher proportion of subjects having fibrosis improvement (i.e. decrease > or = to 1 point) without a worsening of NASH, compared to subjects treated with a placebo. The improvement ratio is at least 2 when compared to subjects treated with a placebo.

Treatment with 400 mg of Aramchol results in a significantly higher proportion of subjects with NAS Score improvement (i.e. improvement of at least 2 points) without worsening of fibrosis score, compared to subjects treated with a placebo.

Treatment with 400 mg of Aramchol results in a significantly higher proportion of subjects with SAF Activity score improvement (i.e. improvement of at least 2 points) without worsening of fibrosis score, compared to subjects treated with a placebo.

Treatment with 400 mg of Aramchol results in a significantly higher proportion of subjects with NASH resolution (ballooning of 0, inflammation of 0 or 1) without worsening of fibrosis, compared to subjects treated with a placebo.
Exploratory Outcome Measures (400 mg Arm)

Treatment with 400 mg of Aramchol inhibits worsening of the subject's fibrosis score significantly more than what would be expected based on Aramchol's effect on the subject's liver triglycerides.

Treatment with 400 mg of Aramchol to subjects afflicted with hepatic fibrosis improves the subject's fibrosis score significantly more than what would be expected based on Aramchol's effect on the subject's liver triglycerides.

Treatment with 400 mg of Aramchol to subjects afflicted with stage 1a hepatic fibrosis improves the subject's fibrosis score significantly more than the effect that would be expected based on Aramchol's effect on the subject's liver triglycerides.

Treatment with 400 mg of Aramchol to subjects afflicted with stage 1b hepatic fibrosis improves the subject's fibrosis score significantly more than the effect that would be expected based on Aramchol's effect on the subject's liver triglycerides.

Treatment with 400 mg of Aramchol to subjects afflicted with stage 1c hepatic fibrosis improves the subject's fibrosis score significantly more than the effect that would be expected based on Aramchol's effect on the subject's liver triglycerides.

Treatment with 400 mg of Aramchol to subjects afflicted with stage 2 hepatic fibrosis improves the subject's fibrosis score significantly more than the effect that would be expected based on Aramchol's effect on the subject's liver triglycerides.

Treatment with 400 mg of Aramchol to subjects afflicted with stage 3 hepatic fibrosis improves the subject's fibrosis score significantly more than the effect that would be expected based on Aramchol's effect on the subject's liver triglycerides.

Treatment with 400 mg of Aramchol to subjects afflicted with stage 4 hepatic fibrosis improves the subject's fibrosis score significantly more than the effect that would be expected based on Aramchol's effect on the subject's liver triglycerides.

Treatment with 400 mg of Aramchol to subjects afflicted with hepatic fibrosis improves the subject's SAF score more than what would be expected based on Aramchol's effect on the subject's liver triglycerides.

Treatment with 400 mg of Aramchol to subjects afflicted with hepatic fibrosis results in a significantly higher proportion of subjects without worsening of fibrosis score, compared to subjects afflicted with hepatic fibrosis treated with a placebo.

Treatment with 400 mg of Aramchol to subjects afflicted with hepatic fibrosis results in a significantly higher proportion of subjects having fibrosis improvement (i.e. decrease > or = to 1 point), compared to subjects afflicted with hepatic fibrosis treated with a placebo.

Treatment with 400 mg of Aramchol to subjects afflicted with hepatic fibrosis results in a significantly higher proportion of subjects having fibrosis improvement (i.e. decrease > or = to 1 point) without a worsening of NASH, compared to subjects afflicted with hepatic fibrosis treated with a placebo.

Treatment with 400 mg of Aramchol to subjects afflicted with hepatic fibrosis results in a significantly higher proportion of subjects having fibrosis improvement (i.e. decrease > or = to 1 point) without a worsening of NASH, compared to subjects treated with a placebo. The improvement ratio is at least 2 when compared to subjects afflicted with hepatic fibrosis treated with a placebo.

Treatment with 400 mg of Aramchol results in a significantly higher proportion of subjects with NAS Score improvement (i.e. improvement of at least 2 points) compared to subjects afflicted with hepatic fibrosis treated with a placebo.

Treatment with 400 mg of Aramchol results in a significantly higher proportion of subjects with NAS Score improvement (i.e. improvement of at least 2 points) without worsening of fibrosis score, compared to subjects afflicted with hepatic fibrosis treated with a placebo.

Treatment with 400 mg of Aramchol to subjects afflicted with hepatic fibrosis results in a significantly higher proportion of subjects with SAF Activity score improvement (i.e. improvement of at least 2 points) compared to subjects afflicted with hepatic fibrosis treated with a placebo.

Treatment with 400 mg of Aramchol to subjects afflicted with hepatic fibrosis results in a significantly higher proportion of subjects with SAF Activity score improvement (i.e. improvement of at least 2 points) without worsening of fibrosis score, compared to subjects afflicted with hepatic fibrosis treated with a placebo.

Treatment with 400 mg of Aramchol to subjects afflicted with hepatic fibrosis results in a significantly higher proportion of subjects with NASH resolution (ballooning of 0, inflammation of 0 or 1) compared to subjects afflicted with hepatic fibrosis treated with a placebo.

Treatment with 400 mg of Aramchol to subjects afflicted with hepatic fibrosis results in a significantly higher proportion of subjects with NASH resolution (ballooning of 0, inflammation of 0 or 1) without worsening of fibrosis, compared to subjects afflicted with hepatic fibrosis treated with a placebo.

Treatment with 400 mg of Aramchol to subjects not afflicted with hepatic fibrosis results in a significantly higher proportion of subjects without worsening of fibrosis score, compared to subjects not afflicted with hepatic fibrosis treated with a placebo.

Treatment with 400 mg of Aramchol results in a significantly higher proportion of subjects with NAS Score improvement (i.e. improvement of at least 2 points) compared to subjects not afflicted with hepatic fibrosis treated with a placebo.

Treatment with 400 mg of Aramchol results in a significantly higher proportion of subjects with NAS Score improvement (i.e. improvement of at least 2 points) without worsening of fibrosis score, compared to subjects not afflicted with hepatic fibrosis treated with a placebo.

Treatment with 400 mg of Aramchol to subjects not afflicted with hepatic fibrosis results in a significantly higher proportion of subjects with SAF Activity score improvement (i.e. improvement of at least 2 points) compared to subjects not afflicted with hepatic fibrosis treated with a placebo.

Treatment with 400 mg of Aramchol to subjects not afflicted with hepatic fibrosis results in a significantly higher proportion of subjects with SAF Activity score improvement (i.e. improvement of at least 2 points) without worsening of fibrosis score, compared to subjects not afflicted with hepatic fibrosis treated with a placebo.

Treatment with 400 mg of Aramchol to subjects not afflicted with hepatic fibrosis results in a significantly higher proportion of subjects with NASH resolution (ballooning of 0, inflammation of 0 or 1) compared to subjects not afflicted with hepatic fibrosis treated with a placebo.

Treatment with 400 mg of Aramchol to subjects not afflicted with hepatic fibrosis results in a significantly higher proportion of subjects with NASH resolution (ballooning of 0, inflammation of 0 or 1) without worsening of fibrosis, compared to subjects not afflicted with hepatic fibrosis treated with a placebo.

Primary and Secondary Outcome Measures (600 mg Arm)

Treatment with 600 mg of Aramchol significantly reduces liver triglycerides ratio as measured by Magnetic Resonance Spectroscopy (MRS).

Treatment with 600 mg of Aramchol reduces liver triglycerides ratio as measured by Magnetic Resonance Spectroscopy (MRS) by 10-40%.

Treatment with 600 mg of Aramchol reduces liver triglycerides ratio as measured by Magnetic Resonance Spectroscopy (MRS) by 15%-35%.

Treatment with 600 mg of Aramchol reduces liver triglycerides ratio as measured by Magnetic Resonance Spectroscopy (MRS) by 20%-30%.

Treatment with 600 mg of Aramchol results in a significantly higher proportion of subjects having fibrosis improvement (i.e. decrease > or = to 1 point) without a worsening of NASH, compared to subjects treated with a placebo.

Treatment with 600 mg of Aramchol results in a significantly higher proportion of subjects having fibrosis improvement (i.e. decrease > or = to 1 point) without a worsening of NASH, compared to subjects treated with a placebo. The improvement ratio is at least 2 when compared to subjects treated with a placebo.

Treatment with 600 mg of Aramchol results in a significantly higher proportion of subjects with NAS Score improvement (i.e. improvement of at least 2 points) without worsening of fibrosis score, compared to subjects treated with a placebo.

Treatment with 600 mg of Aramchol results in a significantly higher proportion of subjects with SAF Activity score improvement (i.e. improvement of at least 2 points) without worsening of fibrosis score, compared to subjects treated with a placebo.

Treatment with 600 mg of Aramchol results in a significantly higher proportion of subjects with NASH resolution (ballooning of 0, inflammation of 0 or 1) without worsening of fibrosis, compared to subjects treated with a placebo.

Exploratory Outcome Measures (600 mg Arm)

Treatment with 600 mg of Aramchol inhibits worsening of the subject's fibrosis score significantly more than what would be expected based on Aramchol's effect on the subject's liver triglycerides.

Treatment with 600 mg of Aramchol to subjects afflicted with hepatic fibrosis improves the subject's fibrosis score significantly more than what would be expected based on Aramchol's effect on the subject's liver triglycerides.

Treatment with 600 mg of Aramchol to subjects afflicted with stage 1a hepatic fibrosis improves the subject's fibrosis score significantly more than the effect that would be expected based on Aramchol's effect on the subject's liver triglycerides.

Treatment with 600 mg of Aramchol to subjects afflicted with stage 1b hepatic fibrosis improves the subject's fibrosis score significantly more than the effect that would be expected based on Aramchol's effect on the subject's liver triglycerides.

Treatment with 600 mg of Aramchol to subjects afflicted with stage 1c hepatic fibrosis improves the subject's fibrosis score significantly more than the effect that would be expected based on Aramchol's effect on the subject's liver triglycerides.

Treatment with 600 mg of Aramchol to subjects afflicted with stage 2 hepatic fibrosis improves the subject's fibrosis score significantly more than the effect that would be expected based on Aramchol's effect on the subject's liver triglycerides.

Treatment with 600 mg of Aramchol to subjects afflicted with stage 3 hepatic fibrosis improves the subject's fibrosis score significantly more than the effect that would be expected based on Aramchol's effect on the subject's liver triglycerides.

Treatment with 600 mg of Aramchol to subjects afflicted with stage 4 hepatic fibrosis improves the subject's fibrosis score significantly more than the effect that would be expected based on Aramchol's effect on the subject's liver triglycerides.

Treatment with 600 mg of Aramchol to subjects afflicted with hepatic fibrosis improves the subject's SAF score more than what would be expected based on Aramchol's effect on the subject's liver triglycerides.

Treatment with 600 mg of Aramchol to subjects afflicted with hepatic fibrosis results in a significantly higher proportion of subjects without worsening of fibrosis score, compared to subjects afflicted with hepatic fibrosis treated with a placebo.

Treatment with 600 mg of Aramchol to subjects afflicted with hepatic fibrosis results in a significantly higher proportion of subjects having fibrosis improvement (i.e. decrease > or = to 1 point), compared to subjects afflicted with hepatic fibrosis treated with a placebo.

Treatment with 600 mg of Aramchol to subjects afflicted with hepatic fibrosis results in a significantly higher proportion of subjects having fibrosis improvement (i.e. decrease > or = to 1 point) without a worsening of NASH, compared to subjects afflicted with hepatic fibrosis treated with a placebo.

Treatment with 600 mg of Aramchol to subjects afflicted with hepatic fibrosis results in a significantly higher proportion of subjects having fibrosis improvement (i.e. decrease > or = to 1 point) without a worsening of NASH, compared to subjects treated with a placebo. The improvement ratio is at least 2 when compared to subjects afflicted with hepatic fibrosis treated with a placebo.

Treatment with 600 mg of Aramchol results in a significantly higher proportion of subjects with NAS Score improvement (i.e. improvement of at least 2 points) compared to subjects afflicted with hepatic fibrosis treated with a placebo.

Treatment with 600 mg of Aramchol results in a significantly higher proportion of subjects with NAS Score improvement (i.e. improvement of at least 2 points) without worsening of fibrosis score, compared to subjects afflicted with hepatic fibrosis treated with a placebo.

Treatment with 600 mg of Aramchol to subjects afflicted with hepatic fibrosis results in a significantly higher proportion of subjects with SAF Activity score improvement (i.e. improvement of at least 2 points) compared to subjects afflicted with hepatic fibrosis treated with a placebo.

Treatment with 600 mg of Aramchol to subjects afflicted with hepatic fibrosis results in a significantly higher proportion of subjects with SAF Activity score improvement (i.e. improvement of at least 2 points) without worsening of fibrosis score, compared to subjects afflicted with hepatic fibrosis treated with a placebo.

Treatment with 600 mg of Aramchol to subjects afflicted with hepatic fibrosis results in a significantly higher proportion of subjects with NASH resolution (ballooning of 0, inflammation of 0 or 1) compared to subjects afflicted with hepatic fibrosis treated with a placebo.

Treatment with 600 mg of Aramchol to subjects afflicted with hepatic fibrosis results in a significantly higher proportion of subjects with NASH resolution (ballooning of 0, inflammation of 0 or 1) without worsening of fibrosis, compared to subjects afflicted with hepatic fibrosis treated with a placebo.

Treatment with 600 mg of Aramchol to subjects not afflicted with hepatic fibrosis results in a significantly higher proportion of subjects without worsening of fibrosis score, compared to subjects not afflicted with hepatic fibrosis treated with a placebo.

Treatment with 600 mg of Aramchol results in a significantly higher proportion of subjects with NAS Score improvement (i.e. improvement of at least 2 points) compared to subjects not afflicted with hepatic fibrosis treated with a placebo.

Treatment with 600 mg of Aramchol results in a significantly higher proportion of subjects with NAS Score improvement (i.e. improvement of at least 2 points) without worsening of fibrosis score, compared to subjects not afflicted with hepatic fibrosis treated with a placebo.

Treatment with 600 mg of Aramchol to subjects not afflicted with hepatic fibrosis results in a significantly higher proportion of subjects with SAF Activity score improvement (i.e. improvement of at least 2 points) compared to subjects not afflicted with hepatic fibrosis treated with a placebo.

Treatment with 600 mg of Aramchol to subjects not afflicted with hepatic fibrosis results in a significantly higher proportion of subjects with SAF Activity score improvement (i.e. improvement of at least 2 points) without worsening of fibrosis score, compared to subjects not afflicted with hepatic fibrosis treated with a placebo.

Treatment with 600 mg of Aramchol to subjects not afflicted with hepatic fibrosis results in a significantly higher proportion of subjects with NASH resolution (ballooning of 0, inflammation of 0 or 1) compared to subjects not afflicted with hepatic fibrosis treated with a placebo.

Treatment with 600 mg of Aramchol to subjects not afflicted with hepatic fibrosis results in a significantly higher proportion of subjects with NASH resolution (ballooning of 0, inflammation of 0 or 1) without worsening of fibrosis, compared to subjects not afflicted with hepatic fibrosis treated with a placebo.

Discussion

Based on studies described herein, Aramchol is surprisingly found to be a potent anti-fibrotic and anti-cirrhotic agent. Aramchol is also found to be unexpectedly superior to OCA and provides improved, effective treatment for liver fibrosis. Accordingly, Aramchol may be used to prevent acute or fatal liver failure and/or hepatic or portosystemic encephalopathy, for example toxin-induced liver failure and/or hepatic encephalopathy.

Furthermore, Aramchol is also surprisingly found to be effective in reversing established fibrosis. Aramchol treatment improves liver histology as determined by a reduction of lipid accumulation (Sudan red staining), fibrosis (Sirius red and SMA staining) and inflammation (F4/80 and CD64 staining). Indeed, Aramchol has an effect on fibrosis in addition to main pathologies of NASH, namely steatosis and inflammation.

Results presented herein show that Aramchol down-regulates collagen production from human stellate cells, the effects of Aramchol are mediated through down regulation of SCD 1 and up regulation of glutathione production, and the effect of Aramchol on fibrosis is mediated via down regulation of steatosis and inflammation as well as directly via down regulation of collagen production from stellate cells. Taken together, information herein supports the effects of Aramchol in human patients as set forth in the claims.

Results analogous to those of Example 4 for 400 mg or 600 mg doses are expected for higher doses of Aramchol that are recited herein.

What is claimed is:

1. A method of treating hepatic fibrosis in a human subject afflicted with hepatic fibrosis, comprising administering to the subject greater than 300 mg per day of a 3β-arachidylamido-7α, 12α-dihydroxy-5β-cholan-24-oic acid (Aramchol), or a pharmaceutically acceptable salt thereof, wherein the treatment of hepatic fibrosis comprises down regulation of collagen production in the liver of said subject, thereby treating hepatic fibrosis in said subject; and wherein the hepatic fibrosis being caused by contact with a hepatotoxic chemical substance or by mechanical obstruction, malnutrition, hemochromatosis, passive congestion, exposure to poisons or toxins, exposure to drugs, immune reactions, genetically determined sensitivities to a certain substance, infections, syphilis, autoimmune hepatitis, toxin-induced hepatitis, storage or metabolism hepatic disorders, congenital hepatic fibrosis, primary biliary cirrhosis, drug-induced hepatitis, parasitic hepatitis, primary sclerosing cholangitis, Budd-Chiari syndrome, hepatic veno-occlusive disease, portal vein thrombosis, or scarring due to prior liver surgery, or wherein said fibrosis is manifested by portal hypertension and/or hepatic cirrhosis, and wherein the hepatic fibrosis is associated with a disorder other than non-alcoholic fatty liver disease and/or non-alcoholic steatohepatitis.

2. The method of claim 1, wherein 400 mg, 600 mg or 800 mg of Aramchol is administered to the subject per day.

3. The method of claim 1 wherein the Aramchol is administered with water, or at the same time as, or within 30 minutes of a meal;
   wherein the meal is breakfast, lunch, or dinner, or
   wherein the meal is a high fat meal or a high calorie meal.

4. The method of claim 1, wherein the Aramchol is administered over the course of at least 40 weeks, at least 52 weeks, at least 72 weeks, at least 96 weeks, at least 2 years, at least 3 years, or at least 4 years.

5. The method of claim 1, wherein the human subject has a diet that is high fat and high calorie; and/or
   is resistant to lifestyle intervention
   or is resistant to diet intervention.

6. The method of claim 1, further comprising administering a therapeutically effect amount of a pharmaceutical composition comprising at least one compound selected from the group consisting of:
   a) ethyl eicosapentanoate (EPA-E), eicosapentaenoic acid (EPA) and its pharmaceutically acceptable amides, salts, esters and phospholipids;
   b) an inhibitor of Acetyl-CoA carboxylase (ACC) alone, or in combination with one or more additional therapeutic agents;
   c) pioglitazone hydrochloride or an enantiopure deuterium-enriched pioglitazone;
   d) a peroxisome proliferator activated receptor (PPAR) delta and gamma dual agonists; and
   e) angiotensin II receptor antagonists, angiotensin converting enzyme (ACE) inhibitors, caspase inhibitors, cathepsin B inhibitors, CCR2 chemokine antagonists, CCR5 chemokine antagonists, chloride channel stimulators, cholesterol solubilizers, diacylglycerol O-acyltransferase 1 (DGAT1) inhibitors, dipeptidyl peptidase IV (DPPIV) inhibitors, farnesoid X receptor (FXR) agonists, FXR/TGR5 dual agonists, galectin-3 inhibitors, LIPC-1010, glucagon-like peptide (GLPI) agonists, glutathione precursors, hepatitis C virus NS3 protease inhibitors, HMG CoA reductase inhibitors, 11-hydroxysteroid dehydrogenase (11-HSD-1) inhibitors, IL-1 antagonists, IL-6 antagonists, IL-10 agonists, IL-17 antagonists, ileal sodium bile acid cotransporter inhibitors, 5 lipoxygenase inhibitors, LPL gene stimulators, lysyl oxidase homolog 2 (LOXL2) inhibitors, PDE3 inhibitors, PDE4 inhibitors, phospholipase C (PLC) inhibitors, PPARa agonists, PPAR gamma agonists, metformin, pentoxyfylline, vitamin E, selenium, omega-3 fatty acids and betaine, PPAR delta agonists, Rho associated protein kinase 2 (ROCK2) inhibitors, sodium glucose transporter-2 (SGLT2) inhibitors, stearoyl CoA desaturase 1 inhibitors, thyroid hormone receptor beta agonists, tumor necrosis factor a (TNFa) ligand inhibitors, transglutaminase inhibitors, transglutaminase inhibitor precursors, PTPib inhibitors, ASKI inhibitors, and vascular adhesion protein-1 inhibitors, PXS4728A, metformin, cysteamine bitartrate, simtuzumab and LUM002,
   wherein
   if said at least one compound is a CCR2 chemokine antagonist then said hepatic fibrosis is caused by any one of:
      contact with a hepatotoxic chemical substance or by mechanical obstruction, malnutrition, hemochromatosis, passive congestion, exposure to poisons or toxins, exposure to drugs, immune reactions, genetically determined sensitivities to a certain substance, syphilis, congenital hepatic fibrosis, Budd-Chiari syndrome, hepatic veno-occlusive disease, portal vein thrombosis, or scarring due to prior liver surgery, or wherein said fibrosis is manifested by portal hypertension and/or hepatic cirrhosis.

7. The method of claim 1, wherein said infection is selected from the group consisting of: bacterial infection, viral infection and parasitic infection.

8. The method of claim 7, wherein said viral infection is viral hepatitis.

9. The method of claim 6, wherein said farnesoid X receptor (FXR) agonists are selected from obeticholic acid and Px-104.

10. The method of claim 6, wherein said galectin-3 inhibitors is GR-MD-02.

11. The method of claim 6, wherein said PPAR gamma agonists are selected from rosiglitazone and pioglitazone.

12. The method of claim 6, wherein said PPAR gamma/delta agonist is GFT-505.

13. The method of claim 6, wherein said PPAR delta agonist is selected from the group consisting of: CER-002, MBX-8025, KD3010 and KD3020.

14. The method of claim 6, wherein said CCR2 or CCR5 chemokine antagonist is cenicriviroc.

* * * * *